US012577398B2

(12) United States Patent
Mihov

(10) Patent No.: US 12,577,398 B2
(45) Date of Patent: Mar. 17, 2026

(54) POLYESTERAMIDE COPOLYMERS POSSESSING HIGH GLASS TRANSITION TEMPERATURES

(71) Applicant: DSM IP Assets B.V., Heerlen (NL)

(72) Inventor: Gueorgui Mihov, Echt (NL)

(73) Assignee: DSM IP ASSETS B.V., Maastricht (NL)

( * ) Notice: Subject to any disclaimer, the term of this patent is extended or adjusted under 35 U.S.C. 154(b) by 853 days.

(21) Appl. No.: 17/774,279

(22) PCT Filed: Nov. 12, 2020

(86) PCT No.: PCT/EP2020/081940
§ 371 (c)(1),
(2) Date: May 4, 2022

(87) PCT Pub. No.: WO2021/094468
PCT Pub. Date: May 20, 2021

(65) Prior Publication Data

US 2022/0396698 A1 Dec. 15, 2022

Related U.S. Application Data

(60) Provisional application No. 62/934,028, filed on Nov. 12, 2019.

(30) Foreign Application Priority Data

Dec. 10, 2019 (EP) .................................... 19214978

(51) Int. Cl.
*C08L 77/12* (2006.01)
*A61K 9/00* (2006.01)
(Continued)

(52) U.S. Cl.
CPC ............ *C08L 77/12* (2013.01); *A61K 9/0051* (2013.01); *A61K 31/5575* (2013.01); *A61K 47/34* (2013.01); *C08L 2203/02* (2013.01)

(58) Field of Classification Search
CPC ... C08L 77/12; C08L 2203/02; A61K 9/0051; A61K 31/5575; A61K 47/34; C08G 69/44
See application file for complete search history.

(56) References Cited

U.S. PATENT DOCUMENTS 4,129,594 A 12/1978 Baker et al.
4,421,787 A 12/1983 Bodor et al.
(Continued)

FOREIGN PATENT DOCUMENTS

CA 2225792 A1 11/1997
CN 1837259 A 9/2006
(Continued)

OTHER PUBLICATIONS

International Search Report and Written Opinion Dated, Feb. 18, 2021.

(Continued)

*Primary Examiner* — Robert C Boyle
(74) *Attorney, Agent, or Firm* — NIXON & VANDERHYE P.C.

(57) ABSTRACT

Disclosed herein are polyesteramide random copolymers having high glass transition temperatures, methods of forming such polymers, devices, formulations, and medical devices containing such polymers, and methods of treating mammals suffering from various conditions using such polymers in combination with a bioactive agent. In an embodiment, the random copolymers may have a Tg above body temperature, about 37° C., and may achieve a longer
(Continued)

release duration, different release kinetics, improved barrier properties, or other benefits over polymers with Tg below 37° C.

21 Claims, 10 Drawing Sheets

(51) Int. Cl.
*A61K 31/5575* (2006.01)
*A61K 47/34* (2017.01)

(56) References Cited

U.S. PATENT DOCUMENTS

| | | | |
|---|---|---|---|
| 4,443,563 | A | 4/1984 | Dirlikov et al. |
| 4,550,730 | A | 11/1985 | Shalaby et al. |
| 4,994,551 | A | 2/1991 | Fung et al. |
| 5,057,313 | A | 10/1991 | Fung et al. |
| 5,091,560 | A | 2/1992 | Rowland |
| 5,100,992 | A | 3/1992 | Cohn et al. |
| 5,133,742 | A | 7/1992 | Cohn et al. |
| 5,206,341 | A | 4/1993 | Pinchuk |
| 5,286,837 | A | 2/1994 | Barrows et al. |
| 5,300,114 | A | 4/1994 | Gwon et al. |
| 5,449,513 | A | 9/1995 | Yokoyama et al. |
| 5,482,700 | A | 1/1996 | Deutsch et al. |
| 5,485,496 | A | 1/1996 | Lee et al. |
| 5,514,379 | A | 5/1996 | Weissleder et al. |
| 5,516,881 | A | 5/1996 | Lee et al. |
| 5,554,692 | A | 9/1996 | Ross |
| 5,583,206 | A | 12/1996 | Snow et al. |
| 5,591,227 | A | 1/1997 | Dinh et al. |
| 5,610,241 | A | 3/1997 | Lee et al. |
| 5,653,998 | A | 8/1997 | Hamann et al. |
| 5,721,131 | A | 2/1998 | Rudolph et al. |
| 5,753,234 | A | 5/1998 | Lee et al. |
| 5,762,939 | A | 6/1998 | Smith et al. |
| 5,770,229 | A | 6/1998 | Tanihara et al. |
| 5,849,841 | A | 12/1998 | Muhlebach et al. |
| 5,852,155 | A | 12/1998 | Bussink et al. |
| 5,858,368 | A | 1/1999 | Smith et al. |
| 5,861,387 | A | 1/1999 | Labrie et al. |
| 5,874,064 | A | 2/1999 | Edwards et al. |
| 5,882,679 | A | 3/1999 | Needham |
| 5,885,491 | A | 3/1999 | Galan Valdivia et al. |
| 5,904,936 | A | 5/1999 | Huille et al. |
| 5,906,934 | A | 5/1999 | Grande et al. |
| 5,916,585 | A | 6/1999 | Cook et al. |
| 5,919,893 | A | 7/1999 | Roby et al. |
| 5,968,794 | A | 10/1999 | Samain et al. |
| 5,972,027 | A | 10/1999 | Johnson |
| 6,004,573 | A | 12/1999 | Rathi et al. |
| 6,103,526 | A | 8/2000 | Smith et al. |
| 6,111,058 | A | 8/2000 | Warzelhan et al. |
| 6,153,252 | A | 11/2000 | Hossainy et al. |
| 6,171,610 | B1 | 1/2001 | Vacanti et al. |
| 6,210,441 | B1 | 4/2001 | Flodin |
| 6,221,997 | B1 | 4/2001 | Woodhouse et al. |
| 6,228,391 | B1 | 5/2001 | Shimizu et al. |
| 6,245,532 | B1 | 6/2001 | Smith et al. |
| 6,299,597 | B1 | 10/2001 | Buscemi et al. |
| 6,342,300 | B1 | 1/2002 | Bengs et al. |
| 6,352,667 | B1 | 3/2002 | English |
| 6,365,160 | B1 | 4/2002 | Webb et al. |
| 6,428,807 | B1 | 8/2002 | MacFarlan et al. |
| 6,476,204 | B1 | 11/2002 | Kim et al. |
| 6,503,538 | B1 | 1/2003 | Chu et al. |
| 6,521,431 | B1 | 2/2003 | Kiser et al. |
| 6,541,606 | B2 | 4/2003 | Margolin et al. |
| 6,660,525 | B2 | 12/2003 | Martin et al. |
| 6,703,040 | B2 | 3/2004 | Katsarava et al. |
| 6,716,445 | B2 | 4/2004 | Won et al. |
| 6,793,938 | B2 | 9/2004 | Sankaram |
| 6,830,747 | B2 | 12/2004 | Lang et al. |
| 6,982,249 | B1 | 1/2006 | Schmaier et al. |
| 6,984,393 | B2 | 1/2006 | Amsden |
| 6,994,867 | B1 | 2/2006 | Hossainy et al. |
| 7,026,156 | B1 | 4/2006 | Clark et al. |
| 7,041,785 | B1 | 5/2006 | Recoli et al. |
| 7,122,202 | B2 | 10/2006 | Allen et al. |
| 7,220,816 | B2 | 5/2007 | Pacetti et al. |
| 7,304,122 | B2 | 12/2007 | Chu et al. |
| 7,408,018 | B2 | 8/2008 | Chu et al. |
| 7,538,180 | B2 | 5/2009 | Pacetti et al. |
| 7,649,022 | B2 | 1/2010 | Gomurashvili et al. |
| 7,658,727 | B1 | 2/2010 | Fernandes et al. |
| 7,670,829 | B2 | 3/2010 | Spagnoli et al. |
| 7,744,861 | B2 | 6/2010 | Zhao et al. |
| 7,776,240 | B2 | 8/2010 | Chu et al. |
| 7,785,618 | B2 | 8/2010 | Elmaleh et al. |
| 7,794,494 | B2 | 9/2010 | Sahatjian et al. |
| 7,794,706 | B2 | 9/2010 | Carpenter et al. |
| 7,863,406 | B2 | 1/2011 | Chu et al. |
| 7,935,493 | B2 | 5/2011 | Michnick et al. |
| 8,067,031 | B2 | 11/2011 | Daniloff et al. |
| 8,163,269 | B2 | 4/2012 | Carpenter et al. |
| 9,873,764 | B2 | 1/2018 | Mihov |
| 9,873,765 | B2 | 1/2018 | Draaisma |
| 9,896,544 | B2 | 2/2018 | Draaisma |
| 9,963,549 | B2 | 5/2018 | Draaisma |
| 10,538,864 | B2 | 1/2020 | Gillissen-van Der Vight et al. |
| 2001/0038851 | A1 | 11/2001 | Allen et al. |
| 2002/0015720 | A1 | 2/2002 | Katsarava et al. |
| 2002/0034532 | A1 | 3/2002 | Brodbeck et al. |
| 2002/0044972 | A1 | 4/2002 | Davis et al. |
| 2002/0049495 | A1 | 4/2002 | Kutryk et al. |
| 2002/0106369 | A1 | 8/2002 | Horvath et al. |
| 2002/0147296 | A1 | 10/2002 | Teller et al. |
| 2002/0164374 | A1 | 11/2002 | Jackson et al. |
| 2002/0165347 | A1 | 11/2002 | Fox et al. |
| 2002/0168338 | A1 | 11/2002 | Baird |
| 2002/0173586 | A1 | 11/2002 | Jeong et al. |
| 2003/0064053 | A1 | 4/2003 | Liu et al. |
| 2003/0130185 | A1 | 7/2003 | Bar-Or et al. |
| 2003/0175239 | A1 | 9/2003 | Margolin et al. |
| 2003/0215454 | A1 | 11/2003 | Colb et al. |
| 2003/0217748 | A1 | 11/2003 | Giroux |
| 2003/0229393 | A1 | 12/2003 | Kutryk et al. |
| 2004/0017387 | A1 | 1/2004 | Soltero et al. |
| 2004/0024069 | A1 | 2/2004 | Chen et al. |
| 2004/0057958 | A1 | 3/2004 | Waggoner, Jr. et al. |
| 2004/0063606 | A1 | 4/2004 | Chu et al. |
| 2004/0110285 | A1 | 6/2004 | Lendlein et al. |
| 2004/0170685 | A1 | 9/2004 | Carpenter et al. |
| 2004/0213759 | A1 | 10/2004 | Zalipsky et al. |
| 2004/0213766 | A1 | 10/2004 | Francois |
| 2004/0253293 | A1 | 12/2004 | Shafiee et al. |
| 2004/0254151 | A1 | 12/2004 | Ralston et al. |
| 2004/0258702 | A1 | 12/2004 | Blonder et al. |
| 2005/0004378 | A1 | 1/2005 | Mane et al. |
| 2005/0013812 | A1 | 1/2005 | Dow et al. |
| 2005/0019366 | A1 | 1/2005 | Zeldis |
| 2005/0019404 | A1 | 1/2005 | Sung et al. |
| 2005/0025752 | A1 | 2/2005 | Kutryk et al. |
| 2005/0043787 | A1 | 2/2005 | Kutryk et al. |
| 2005/0053667 | A1 | 3/2005 | Irvine et al. |
| 2005/0064602 | A1 | 3/2005 | Kaufman et al. |
| 2005/0169968 | A1 | 8/2005 | Elmaleh et al. |
| 2005/0175583 | A1 | 8/2005 | Tamarkin et al. |
| 2005/0208091 | A1 | 9/2005 | Pacetti |
| 2005/0216074 | A1 | 9/2005 | Sahatjian et al. |
| 2005/0238689 | A1 | 10/2005 | Carpenter et al. |
| 2005/0245637 | A1 | 11/2005 | Hossainy et al. |
| 2005/0260259 | A1 | 11/2005 | Bolotin |
| 2005/0265960 | A1 | 12/2005 | Pacetti et al. |
| 2005/0271700 | A1 | 12/2005 | DesNoyer et al. |
| 2005/0271701 | A1 | 12/2005 | Cottone et al. |
| 2005/0287184 | A1 | 12/2005 | Hossainy et al. |
| 2005/0288481 | A1 | 12/2005 | Desnoyer |
| 2006/0002947 | A1 | 1/2006 | Humphreys et al. |
| 2006/0008532 | A1 | 1/2006 | Govardhan et al. |
| 2006/0009498 | A1 | 1/2006 | Whitcup |
| 2006/0013855 | A1 | 1/2006 | Carpenter et al. |
| 2006/0018948 | A1 | 1/2006 | Guire et al. |

(56) References Cited

U.S. PATENT DOCUMENTS

| | | | | |
|---|---|---|---|---|
| 2006/0024357 | A1 | 2/2006 | Carpenter et al. | |
| 2006/0036311 | A1 | 2/2006 | Nakayama et al. | |
| 2006/0074191 | A1 | 4/2006 | DesNoyer et al. | |
| 2006/0093842 | A1 | 5/2006 | DesNoyer et al. | |
| 2006/0115455 | A1 | 6/2006 | Reed et al. | |
| 2006/0118948 | A1 | 6/2006 | Lin | |
| 2006/0121012 | A1 | 6/2006 | Kutryk et al. | |
| 2006/0135476 | A1 | 6/2006 | Kutryk et al. | |
| 2006/0159918 | A1 | 7/2006 | Dugan et al. | |
| 2006/0177416 | A1 | 8/2006 | Turnell et al. | |
| 2006/0188469 | A1 | 8/2006 | Turnell et al. | |
| 2006/0188486 | A1 | 8/2006 | Carpenter et al. | |
| 2006/0222546 | A1 | 10/2006 | Lee et al. | |
| 2006/0224331 | A1 | 10/2006 | Watson Michnick et al. | |
| 2006/0286064 | A1 | 12/2006 | Turnell et al. | |
| 2007/0042017 | A1 | 2/2007 | Kutryk et al. | |
| 2007/0055367 | A1 | 3/2007 | Kutryk et al. | |
| 2007/0066541 | A1 | 3/2007 | Hughes et al. | |
| 2007/0071790 | A1 | 3/2007 | Ameer et al. | |
| 2007/0077272 | A1 | 4/2007 | Li et al. | |
| 2007/0106035 | A1 | 5/2007 | Gomurashvili et al. | |
| 2007/0128250 | A1 | 6/2007 | Katsarava et al. | |
| 2007/0134332 | A1 | 6/2007 | Turnell et al. | |
| 2007/0141100 | A1 | 6/2007 | Sung et al. | |
| 2007/0141107 | A1 | 6/2007 | Kutryk et al. | |
| 2007/0156232 | A1 | 7/2007 | Kutryk et al. | |
| 2007/0160622 | A1 | 7/2007 | Turnell et al. | |
| 2007/0167605 | A1 | 7/2007 | Chu et al. | |
| 2007/0191932 | A1 | 8/2007 | Kutryk et al. | |
| 2007/0196422 | A1 | 8/2007 | Kutryk et al. | |
| 2007/0213801 | A1 | 9/2007 | Kutryk et al. | |
| 2007/0282011 | A1 | 12/2007 | Gomurashvili et al. | |
| 2007/0287987 | A1 | 12/2007 | Katsarava et al. | |
| 2007/0292476 | A1 | 12/2007 | Landis et al. | |
| 2007/0299155 | A1 | 12/2007 | Carpenter et al. | |
| 2008/0020015 | A1 | 1/2008 | Carpenter et al. | |
| 2008/0050419 | A1 | 2/2008 | Katsarava et al. | |
| 2008/0057024 | A1 | 3/2008 | Zhang et al. | |
| 2008/0160089 | A1 | 7/2008 | Vitiello et al. | |
| 2008/0288057 | A1 | 11/2008 | Carpenter et al. | |
| 2008/0299174 | A1* | 12/2008 | Gomurashvili | A61P 9/00 525/410 |
| 2008/0314289 | A1 | 12/2008 | Pham | |
| 2009/0022772 | A1 | 1/2009 | Carpenter | |
| 2009/0029937 | A1 | 1/2009 | Chu et al. | |
| 2009/0068743 | A1 | 3/2009 | Turnell et al. | |
| 2009/0202620 | A1 | 8/2009 | Turnell et al. | |
| 2009/0232874 | A1 | 9/2009 | Chu et al. | |
| 2009/0238854 | A1 | 9/2009 | Pacetti et al. | |
| 2009/0253809 | A1 | 10/2009 | Gomurashvili et al. | |
| 2010/0004390 | A1 | 1/2010 | Turnell et al. | |
| 2010/0040664 | A1 | 2/2010 | Katsarava et al. | |
| 2011/0027379 | A1 | 2/2011 | Chu et al. | |
| 2011/0137406 | A1 | 6/2011 | Carpenter et al. | |
| 2012/0027859 | A1 | 2/2012 | Turnell et al. | |
| 2012/0282299 | A1 | 11/2012 | Delamarre et al. | |
| 2012/0328706 | A1 | 12/2012 | Turnell et al. | |
| 2014/0105957 | A1 | 4/2014 | Franken et al. | |
| 2014/0120170 | A1* | 5/2014 | Mihov | A61P 9/00 424/501 |
| 2014/0179802 | A1* | 6/2014 | Franken | A61K 9/0019 528/321 |
| 2014/0220099 | A1 | 8/2014 | Draaisma et al. | |
| 2015/0038415 | A1 | 2/2015 | Zupancich | |
| 2015/0216987 | A1 | 8/2015 | Thies et al. | |
| 2015/0240387 | A1 | 8/2015 | Gillissen-Van Der Vight et al. | |
| 2015/0246001 | A1 | 9/2015 | Zupancich et al. | |
| 2015/0328374 | A1 | 11/2015 | Zupancich et al. | |

FOREIGN PATENT DOCUMENTS

| | | | |
|---|---|---|---|
| CN | 101168595 | A1 | 4/2008 |
| EP | 0396429 | A2 | 11/1990 |
| EP | 0447719 | A1 | 9/1991 |
| EP | 0926184 | A1 | 6/1999 |
| EP | 0932399 | A1 | 8/1999 |
| JP | 2005139139 | | 6/2005 |
| JP | 2009-513783 | | 4/2009 |
| WO | 1994004642 | A2 | 3/1994 |
| WO | 1997030104 | A1 | 8/1997 |
| WO | 1998032398 | A1 | 7/1998 |
| WO | 9929303 | | 6/1999 |
| WO | 99029302 | | 6/1999 |
| WO | 1999058151 | A2 | 11/1999 |
| WO | 1999061916 | A1 | 12/1999 |
| WO | 2001051027 | A2 | 7/2001 |
| WO | 2001091703 | A2 | 12/2001 |
| WO | 0218477 | A2 | 3/2002 |
| WO | 2002018477 | A2 | 3/2002 |
| WO | 03024420 | A1 | 3/2003 |
| WO | 2003062298 | A1 | 7/2003 |
| WO | 2004039944 | A2 | 5/2004 |
| WO | 2004040339 | A1 | 5/2004 |
| WO | 2005027906 | A1 | 3/2005 |
| WO | 2005061024 | A1 | 7/2005 |
| WO | 2005097186 | A2 | 10/2005 |
| WO | 2005112587 | A2 | 12/2005 |
| WO | 2005112884 | A1 | 12/2005 |
| WO | 2005118681 | A2 | 12/2005 |
| WO | 2006050091 | A2 | 5/2006 |
| WO | 2006083874 | A2 | 8/2006 |
| WO | 2006088647 | A1 | 8/2006 |
| WO | 2006108167 | A1 | 10/2006 |
| WO | 2006132950 | A2 | 12/2006 |
| WO | 2007035938 | A2 | 3/2007 |
| WO | 2007038246 | A2 | 4/2007 |
| WO | 2007/050583 | | 5/2007 |
| WO | 2007067744 | A1 | 6/2007 |
| WO | 2007089870 | A2 | 8/2007 |
| WO | 2007089931 | A1 | 8/2007 |
| WO | 2007130477 | A2 | 11/2007 |
| WO | 2007133616 | A2 | 11/2007 |
| WO | 2008048298 | A2 | 4/2008 |
| WO | 2008157254 | A2 | 12/2008 |
| WO | 2009012449 | A1 | 1/2009 |
| WO | 2009015143 | A1 | 1/2009 |
| WO | 2009026543 | | 4/2009 |
| WO | 20100045241 | | 4/2009 |
| WO | 2011045443 | | 4/2011 |
| WO | 2011146483 | | 11/2011 |
| WO | 2012150255 | | 11/2012 |
| WO | 2012175746 | | 12/2012 |
| WO | 2012175746 | A1 | 12/2012 |
| WO | 2012175748 | | 12/2012 |
| WO | 2014064196 | A1 | 5/2014 |
| WO | 2014096339 | A1 | 6/2014 |

OTHER PUBLICATIONS

Notice of Reasons for Rejection, JP Application No. P2022-521406, Nov. 26, 2024 (with English-language translation).

Zaza Gomurashvili et al, "Form Drug-Eluting Stents to Biopharmaceuticals: Poly(ester amide) a Versatile New Bioabsorbable Biopolymer", Polymers for Biomedical Applications ACS Symposium Series; American Chemical Society: Washington, DC, 2008.

Lasín et al, "Sequential Poly(ester amide)s Based on Glycine, Diols, and Dicarboxylic Acids: Thermal Polyesterification versus Interfacial Polyamidation. Characterization of Polymers Containing Stiff Units", Journal of Polymer Science: Part A: Polymer Chemistry, vol. 39, 4283-4293 (2001).

James M. Becker et al, "Prevention of Postoperative Abdominal Adhesions By A Sodium Hyaluronate-Based Bioresorbable Membrane: A Prospective, Randomized, Double-Blind Multicenter Study", The Journal of The American College of Surgeons, vol. 183, No. 4, Oct. 1996.

M.E. Eccleston et al, "pH-responsive pseudo-peptides for cell membrane disruption", Journal of Controlled Release 69 (2000) 297-307.

Sandrine Gautier et al, "Alkylated poly(L-lysine citramide) as models to investigate the ability of amphiphilic macromolecular

(56) References Cited

OTHER PUBLICATIONS drug carriers to physically entrap lipophilic compounds in aqueous media", Journal of Controlled Release 60 (1999) 235-247.
Z.Gomurashvili et al, "Amino Acid Based Bloanalogous Polymers. Synthesis and Study of New Poly(ester amide)s Composed of Hydrophobic α-Amino Acids and Dianhydrohexitoles", Journal of Macromolecular Science—Pure Appl. Chem., A37(3), pp. 215-227 (2000).
M.E. Eccleston et al, "Synthetic routes to responsive polymers; co-polycondensation of tri-functional amino acids with diacylchlorides", Reactive & Functional Polymers 42 (1999) 147-161.
R.F. Furchgott et al, "The obligatory role of endothelial cells in the relaxation of arterial smooth muscle by acetylcholine", Nature, vol. 288, pp. 373-376, Nov. 27, 1980.
Tamara Katvelishvili et al, "Amno acid based bioanalogous polymers. Novel regular poly(ester urethane)s and poly(ester urea)s based on bis(L-phenylalanine) α,ω-alkylene diesters", Macromol. Chem.Phys. 198, 1921-1932 (1977).
Zhiyong Qian et al, "Preparation of biodegradable polyesteramide microspheres", Colloid Polym. Sci. (2004) 282: 1083-1088.
Kai Guo et al, "Synthesis and Characterization of Novel Biodegradable Unsaturated Poly(ester amide)/Poly(ethylene glycol) Diacrylate Hydrogels", Journal of Polymer Science: Part A: Polymer Chemistry, vol. 43, 3932-3944 (2005).
Samuel J. Huang et al, "Biodegradable Polymers: Chymotrypsin Degradation of a Low Molecular Wegith Poly(ester-Urea) Containing Phenylalanine", , Journal of Polymer Science, vol. 23, 429-437 (1979).
Yasushi Saotome et al; "Novel Enzymatically Degradable Polymers Comprising α-Amino Acid, 1,2-Ethanediol, and Adipic Acid", The Chemical Society of Japan, Chemistry Letters, pp. 21-24, 1991.
G. Tsitlanadze et al, "Biodegradation of amino-acid-based poly(ester amide)s: in vitro weight loss and preliminary in vivo studies", J. Biomater. Sci. Polymer Edn., vol. 15, No. 1, pp. 1-24 (2004).
Makito Yokoe et al, "Biodegradable Polymers Based on Renewable Resources. VII. Novel Random and Alternating Copolycarbonates from 1,4:3,6-Dianhydrohexitols and Aliphatic Diols", Journal of Polymer Science: Part A: Polymer Chemistry, vol. 41, 2312-2331 (2003).
Notice of Reasons for Rejection, JP Application No. 2022-521406, Jun. 10, 2025.

* cited by examiner 0.3 eqv.
L-leucine(6)-2TosOH 0.45 eqv.
L-leucine(DAS)-2ToSOH 1.00 eqv.
di-N-hydroxysuccinimide ester of sebacic acid 0.25 eqv.
L-lysine(Bz)-2TosOH

POLYESTERAMIDE COPOLYMERS POSSESSING HIGH GLASS TRANSITION TEMPERATURES

CROSS-REFERENCE TO RELATED APPLICATIONS

This application is a U.S. national phase entry under 35 USC 371 of international application PCT/EP2020/081940, filed 12 Nov. 2020, which designated the US and claims priority from U.S. Provisional Application No. 62/934,028, filed 12 Nov. 2019, and European Patent Application No. EP19214978.9, filed 10 Dec. 2019, the entire contents of each of which is hereby incorporated by reference in its entirety.

FIELD

The disclosed inventions pertain to certain polymers, methods of forming such polymers, devices containing such polymers, and methods of treating mammals suffering from various conditions using such polymers in combination with a bioactive agent.

BACKGROUND

Polymers have proven to be useful excipients for the delivery of certain bioactive agents to mammals by injection or implantation. The polymers may be formed into certain shapes or may be present as coatings, depending on the desired method of injection or implantation. The delivery of the bioactive agent occurs when the bioactive agent leaches out of the polymer or when the polymer degrades. Drug delivery devices comprising degradable polymers may be preferred because they may not require a separate procedure to remove the polymer after the bioactive agent is depleted.

However, the use of degradable polymers for drug delivery by injection or implantation has many challenges. For example, achieving the desired release rate for the application, whether burst, zero-order, or some combination of the two, and in combination with a specified release duration, is often challenging. Moreover, certain polymers may be more or less compatible with certain drugs, and this will also affect the release profile. Accordingly, polymers that offer desirable compatibility with certain drugs and that achieve a specific release profile are desirable.

SUMMARY

Numerous properties are important for a polymer to be useful for the delivery of drugs to the body of a mammal. Such properties include the rate at which the polymer degrades, the solubility of the drug in the polymer, and biocompatibility. The barrier properties of a polymer are also important for its function as an excipient in drug delivery formulation. However, the barrier properties when the polymer is below its glass transition temperature (Tg) differ greatly from the barrier properties when the polymer is above its Tg. Moreover, the polymer will be in the "wet" state when present in the body's physiological fluid. Polymers typically have a lower wet Tg than a dry Tg.

Certain biocompatible polymers, such as poly(L-lactic acid) (PLLA), have a wet Tg above body temperature. However, such biocompatible polymers may lack other properties that are more preferred for long-term drug delivery and may be incompatible with certain active pharmaceutical ingredients (APIs).

Other known biocompatible polymers, such as certain polyesteramides (PEAs) may provide better compatibility with certain APIs. However, known PEAs may be plasticized in an aqueous environment and may have a wet Tg below body temperature.

US2008/0299174 discloses a PEA copolymer according to the following Formula IV:

Formula IV

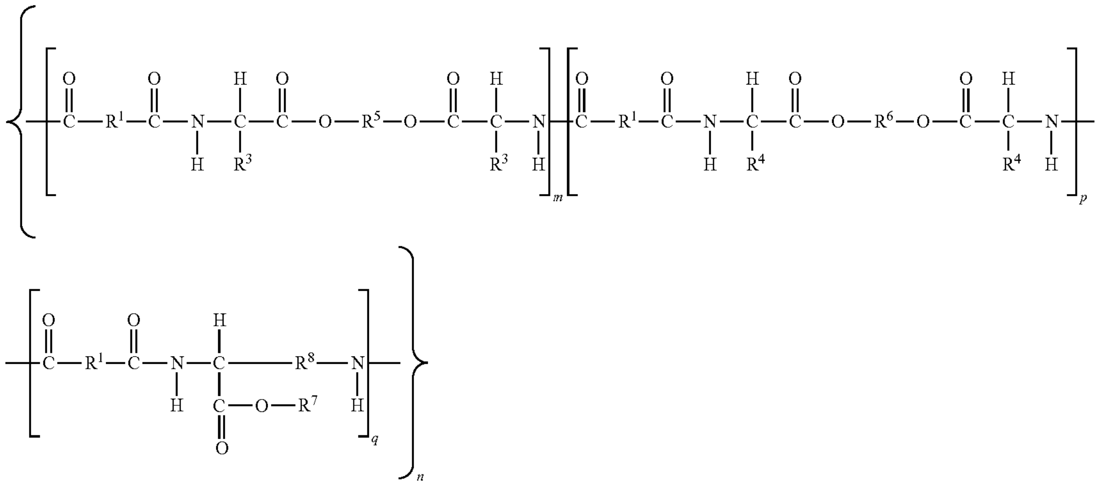

wherein m is about 0.01 to about 0.99, p is about 0.99 to about 0.01, and q is about 0.99 to 0.01, and wherein n is about 5 to about 100; and wherein $R^1$ is independently selected from the group consisting of $(C_2\text{-}C_{20})$alkylene, $(C_2\text{-}C_{20})$alkenylene, and combinations thereof; the $R^3$s and $R^4$s in a single co-monomer m or p, respectively, are independently selected from the group consisting of hydrogen, $(C_1\text{-}C_6)$alkyl, $(C_2\text{-}C_6)$alkenyl, $(C_2\text{-}C_6)$alkynyl, $(C_6\text{-}C_{10})$aryl $(C_1\text{-}C_6)$alkyl and $—(CH_2)_2S(CH_3)$; $R^5$ is selected from bicyclic-fragments of 1,4:3,6-dianhydrohexitols of structural formula (II);

Formula II

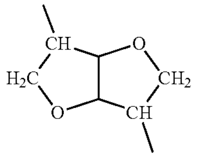

$R^6$ is selected from the group consisting of $(C_2-C_{20})$ alkylene, $(C_2-C_{20})$alkenylene or alkyloxy; $R^7$ is hydrogen, $(C_6-C_{10})$aryl$(C_1-C_6)$alkyl or a protecting group; and $R^8$ is $(C_1-C_{20})$alkyl or $(C_2-C_{20})$alkenyl.

U.S. Pat. No. 9,963,549 discloses a polyesteramide copolymer according to the following Formula V:

Formula V

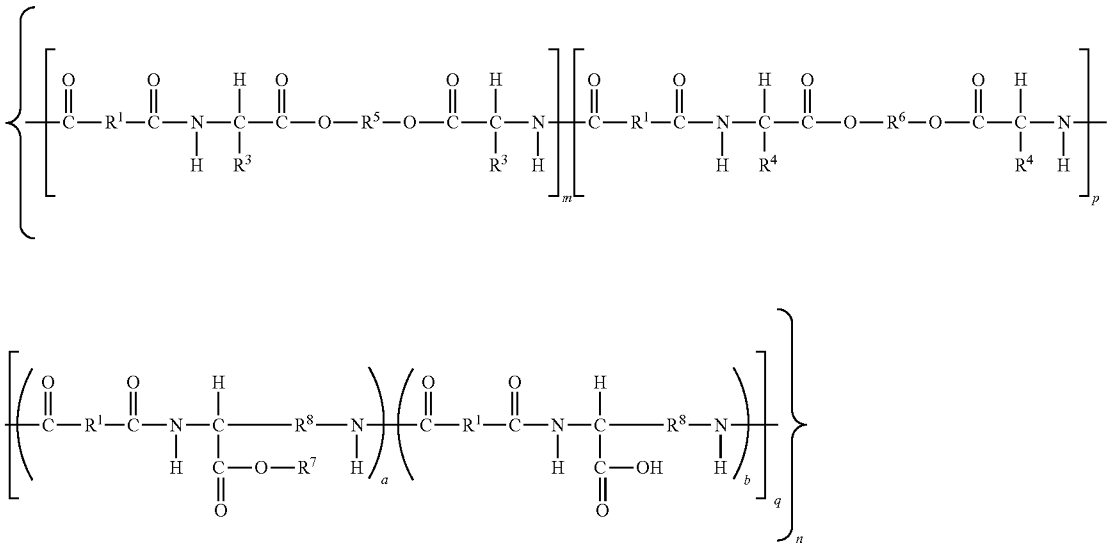

wherein m+p varies from 0.9-0.1 and q varies from 0.1 to 0.9; m+p+q=1 whereby m or p can be 0; and n varies from 5 to 300;

$R^1$ is independently selected from the group consisting of $(C_2-C_{20})$alkylene, $(C_2-C_{20})$ alkenylene, $-(R_9-CO-O-R_{10}-O-CO-R_9)-$, $-CHR_{11}-O-CO-R_{12}-COOCR_{11}-$ and combinations thereof;

$R^3$ and $R^4$ in a single backbone unit m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, $-(CH_2)SH$, $-(CH_2)_2S(CH_3)$, $-CH_2OH$, $-CH(OH)CH_3$, $-(CH_2)_4NH_3+$, $-(CH_2)_3NHC(=NH_2+)NH_2$, $-CH_2COOH$, $-(CH_2)COOH$, $-CH_2-CO-NH_2$, $-CH_2CH_2-CO-NH_2$, $-CH_2CH_2COOH$, $CH_3-CH_2-CH(CH_3)-$, $(CH_3)_2-CH-CH_2-$, $H_2N-(CH_2)_4-$, Ph-$CH_2-$, $CH{=}C-CH_2-$, HO-p-Ph-$CH_2-$, $(CH_3)_2-CH-$, Ph-NH—,

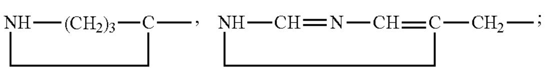

$R^5$ is selected from the group consisting of $(C_2-C_{20})$ alkylene, $(C_2-C_{20})$alkenylene, alkyloxy or oligoethyleneglycol;

$R^6$ is selected from bicyclic-fragments of 1,4:3,6-dianhydrohexitols of structural formula (II);

Formula II

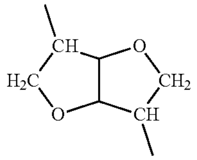

$R^7$ is selected from the group consisting of $(C_6-C_{10})$aryl $(C_1-C_6)$alkyl;

$R_8$ is $-(CH_2)_4-$;

$R_9$ or $R_{10}$ are independently selected from $C_2-C_{12}$ alkylene or $C_2-C_{12}$ alkenylene;

$R_{11}$ or $R_{12}$ are independently selected from H, methyl, $C_2-C_{12}$ alkylene or $C_2-C_{12}$ alkenylene; and whereby a is at least 0.05, b is at least 0.05 and a+b=1.

Having a PEA with a Tg above body temperature, about 37° C., may achieve a longer release duration, different release kinetics, improved barrier properties, or other benefits over PEAs with Tg below 37° C.

In accordance with an embodiment, a random copolymer is according to Formula I:

Formula I

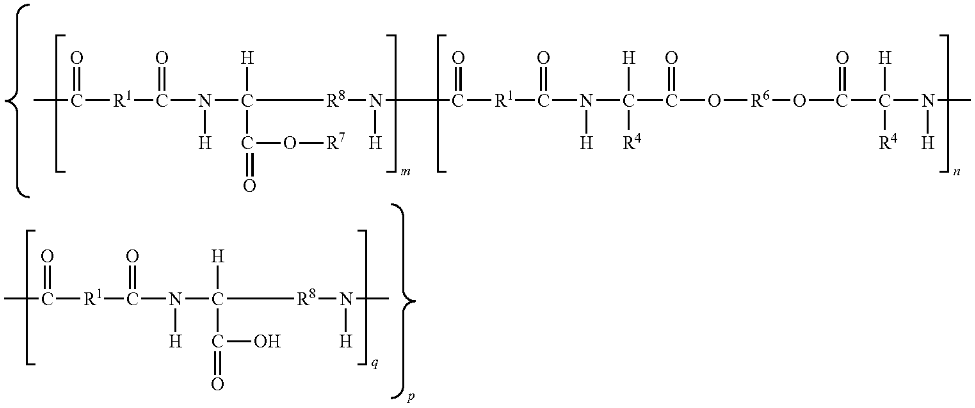

wherein m is from 0 to 0.20, n is from 0.80 to 0.95, q is from 0 to 0.20, and m+n+q=1, wherein m, n, and q represent the equivalents of the corresponding units in the random copolymer;

p is about 5 to about 300;

$R^1$ is $C_2$-$C_{20}$ alkylene;

$R^4$ is hydrogen, $(C_1$-$C_6)$alkyl, $(C_2$-$C_6)$alkenyl, $(C_2$-$C_6)$alkynyl, $(C_6$-$C_{10})$aryl, $—CH_2SH$, $—(CH_2)_2S(CH_3)$, $—CH_2OH$, $—CH(OH)CH_3$, $—(CH_2)_4NH_3+$, $—(CH_2)_3NHC(=NH_2+)NH_2$, $—CH_2COOH$, $—CH_2—CO—NH_2$, $—CH_2CH_2—CO—NH_2$, $—CH_2CH_2COOH$, $CH_3—CH_2—CH(CH_3)—$, $(CH_3)_2CH—CH_2—$, $H_2N—(CH_2)_4—$, $Ph-CH_2—$, $CH≡C—CH_2—$, $(CH_3)_2CH—$, $Ph-NH—$,

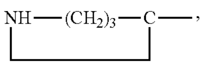, or 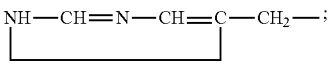;

$R^6$ is according to Formula II or Formula III;

Formula II

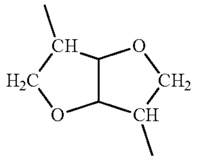

Formula III

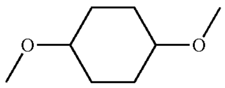

$R^7$ is $(C_6$-$C_{10})$aryl$(C_1$-$C_6)$alkylene; and $R^a$ is $C_3$-$C_8$ alkylene.

The disclosed polymers, implants, and methods may achieve benefits in the release of bioactive agents, such as greater release duration, more uniform daily dose delivery, or a more desirable amount of daily dose, greater compatibility with certain types of bioactive agents, such as acid-sensitive bioactive agents, or improved implant morphology during degradation.

BRIEF DESCRIPTION OF THE DRAWINGS

FIG. 6 is a graph of cumulative release overtime associated with Example 2a.

FIG. 7 is a graph of extrapolated daily dose (µg/day) over time associated with Example 2a.

FIG. 8 is a composite of optical microscopy images at three time periods of a PEA 85D15L X50 implant (2a-2) associated with Example 2a.

FIG. 9 is a composite of optical microscopy images at three time periods of a PEA 85D15L X25 implant (2a-3) associated with Example 2a.

DETAILED DESCRIPTION

Figure 1:
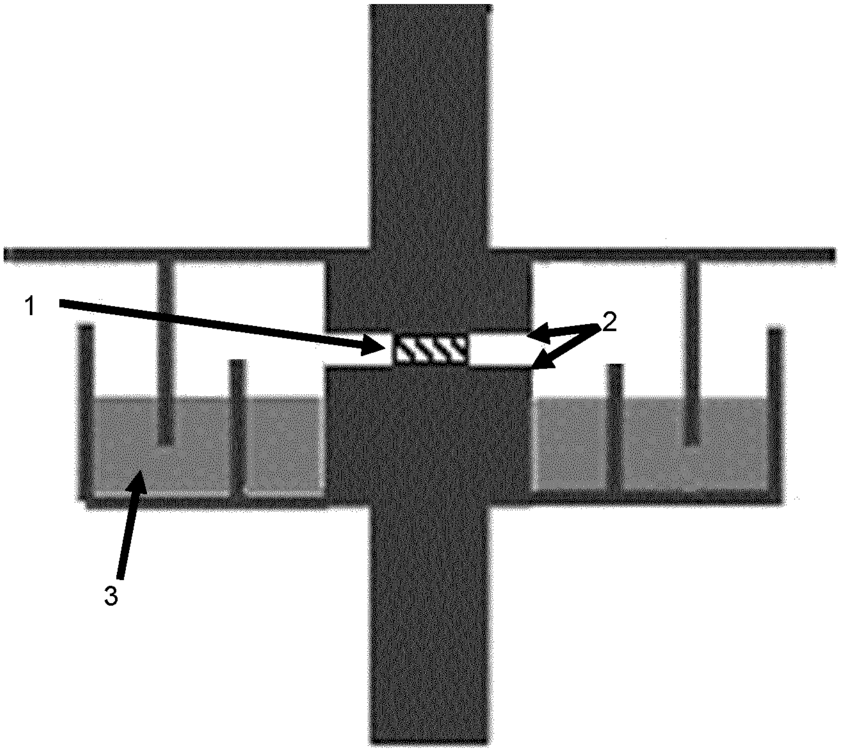
FIG. 1 is a schematic of a wet Tg test apparatus.

In accordance with an embodiment, a random copolymer is according to Formula I:

Formula I

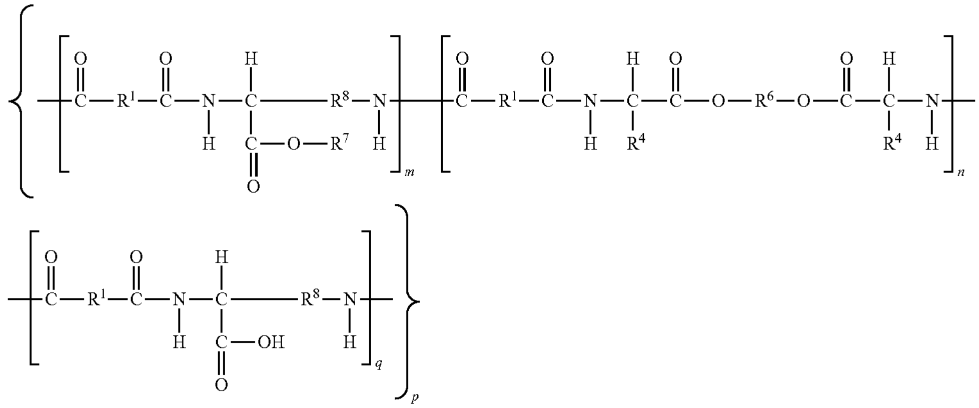

wherein m is from 0 to 0.20, n is from 0.80 to 0.95, q is from 0 to 0.20, and m+n+q=1, wherein m, n, and q represent the equivalents of the corresponding units in the random copolymer;

p is about 5 to about 300;

$R^1$ is $C_2$-$C_{20}$ alkylene;

$R^4$ is hydrogen, $(C_1$-$C_6)$alkyl, $(C_2$-$C_6)$alkenyl, $(C_2$-$C_6)$ alkynyl, $(C_6$-$C_{10})$aryl, $—CH_2SH$, $—(CH_2)_2S(CH_3)$, $—CH_2OH$, $—CH(OH)CH_3$, $—(CH_2)_4NH_3+$, $—(CH_2)_3NHC(=NH_2+)NH_2$, $—CH_2COOH$, $—CH_2—CO—NH_2$, $—CH_2CH_2—CO—NH_2$, $—CH_2CH_2COOH$, $CH_3—CH_2—CH(CH_3)—$, $(CH_3)_2CH—CH_2—$, $H_2N—(CH_2)_4—$, Ph-$CH_2$—, $CH{=}C—CH_2—$, $(CH_3)_2CH—$, Ph-NH—,

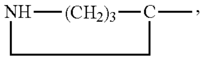 , or 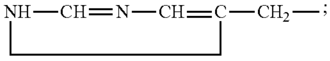 ;

$R^6$ is according to Formula II or Formula III;

Formula II

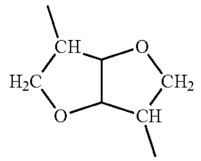

Formula III

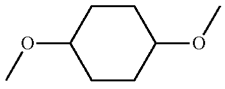

$R^7$ is $(C_6$-$C_{10})$aryl$(C_1$-$C_6)$alkylene; and $R^8$ is $C_3$-$C_8$ alkylene.

As used herein, the term "alkyl" means a monovalent straight or branched chain hydrocarbon group including methyl, ethyl, n-propyl, isopropyl, n-butyl, isobutyl, tert-butyl, n-hexyl, and the like.

As used herein, the term "alkylene" means a divalent branched or unbranched hydrocarbon chain such as $—CH_2—$, $—(CH_2)_2—$, $—(CH_2)_3—$, $—(CH_2)_4—$, $—(CH_2)_5—$, and the like.

As used herein, the term "alkenyl" means a monovalent straight or branched chain hydrocarbon group containing at least one unsaturated bond in the main chain or in a side chain.

As used herein, "alkenylene", means a divalent branched or unbranched hydrocarbon chain containing at least one unsaturated bond in the main chain or in a side chain.

As used herein, "alkynyl", means a straight or branched hydrocarbon chain having at least one carbon-carbon triple bond.

As used herein, "aryl" means a phenyl radical or an ortho-fused bicyclic carbocyclic radical having about nine to ten ring atoms, in which at least one ring is aromatic. Examples of aryl include, but are not limited to, phenyl, naphthyl, and nitrophenyl.

As used herein, "biodegradable" means a material which is capable of being completely or substantially degraded or eroded when exposed to an in vivo environment. A polymer is capable of being degraded or eroded when it can be gradually broken-down, resorbed, absorbed and/or eliminated by, for example, hydrolysis, enzymolysis, oxidation, metabolic processes, bulk or surface erosion, and the like.

As used herein, "random copolymer" means a copolymer wherein two or more individual polymer units are distributed randomly throughout the copolymer. In accordance with Formula I, each of the units m, n, and q are randomly distributed throughout the copolymer.

In an embodiment, n is from 0.80, 0.81, 0.82, 0.825, 0.83, 0.835, 0.84, 0.845, or 0.85 to 0.95, 0.945, 0.94, 0.935, 0.93, 0.925, 0.92, 0.915, 0.91, 0.905, or 0.90. In an embodiment, q is zero. In an embodiment, the ratio of m:q is from 10:1, 9:1, 8:1, 7:1, 6:1, 5:1, 4:1, 3:1, or 2:1 to 1:6, 1:5, 1:4, 1:3, 1:2, or 1:1. In an embodiment, m is greater than or equal to q.

In an embodiment, p is from 5, 10, 15, 20, 25, 30, 35, 40, 45, 50, 55, 60, 65, 70, or 75 to 300, 290, 280, 270, 260, 250, 240, 230, 220, 210, 200, 190, 180, 170, 160, or 150. In an embodiment, the random copolymer of Formula I has a number average molecular weight (Mn) of at least 15,000 g/mol, at least 20,000 g/mol, at least 25,000 g/mol, at least 30,000 g/mol, or at least 35,000 g/mol. In an embodiment, the random copolymer of Formula I has a Mn of at most 250,000 g/mol, at most 225,000 g/mol, at most 200,000 g/mol, at most 175,000 g/mol, at most 150,000 g/mol, at most 125,000 g/mol, at most 100,000 g/mol, or at most 75,000 g/mol. Mn is measured via GPC in THF with polystyrene as standard.

In an embodiment, $R^4$ is hydrogen, $(C_1\text{-}C_6)$alkyl, $CH_3$—$CH_2$—$CH(CH_3)$—, $(CH_3)_2CH$—$CH_2$—, Ph-$CH_2$—, or $(CH_3)_2CH$—. In an embodiment, $R^7$ is $C_6$aryl-$CH_2$— (i.e. benzyl). In an embodiment, $R^8$ is —$(CH_2)_4$—.

Polyesteramide random copolymers are synthesized by adapting a procedure known in the art. R. Katsarava, V. Beridze, N. Arabuli, D. Kharadze, C. C. Chu, C. Y. Won J Polym Sci A: Polym Chem 37: 391-407, 1999. Briefly, the polymers are prepared via solution polycondensation of di-p-toluenesulfonic or hydrochloric acid salts of bis-(α-amino acid) α,ω-diol diesters, lysine benzyl ester, lysine, and/or di-N-hydroxysuccinimide ester of sebacic acid in anhydrous DMSO. Typically, the salts are converted to free amines by addition of triethylamine and these amines are further reacted with the di-acid derivative. The usage of pre-activated acid in the reaction allows polymerization at relatively low temperature, such as 65° C., affording side-product free polycondensates and predictable degradation products. Subsequently, the obtained reaction mixture is purified via a water precipitation followed by an organic precipitation and filtration. Drying under reduced pressure yields the polyesteramide random copolymer.

For example, such polymers may be prepared by reacting lysine, lysine benzyl ester, and hexahydrofuro[3,2-b]furan-3,6-diyl bis(2-amino-4-methylpentanoate) with di-N-hydroxysuccinimide ester activated sebacic acid in DMSO for 24 hours. The polymer is then isolated from the reaction mixture in two precipitation steps and characterized by means of proton NMR and THF-based GPC relative to polystyrene standards.

In an embodiment, the random copolymer according to Formula I has a wet Tg of 36° C. or higher. A wet Tg of 36° C. or higher corresponds to a polymer that may remain solid (glassy) upon injection or implantation into a mammal. In contrast, if the wet Tg is, for example, 32° C. or less, the polymer may behave as a viscous liquid upon injection or implantation. In an embodiment, the random copolymer has a wet Tg of from 36° C., 36.5° C., 37° C., 37.5° C., 38° C., or 39° C. to 45° C., 44° C., 43° C., 42° C., 41° C., 40° C., 39° C., 38° C., or 37° C.

In an embodiment, the initial wet Tg of the random copolymer and the wet Tg of the random copolymer after 35 days in PBS at 37° C. differ by at most +/−10%, +/−9%, +/−8%, +/−7%, +/−6%, or +/−5%. In an embodiment, q is from 0.05 to 0.20, the initial wet Tg of the random copolymer and the wet Tg of the random copolymer after 35 days in PBS at 37° C. differ by at most +/−10%, +/−9%, +/−8%, +/−7%, +/−6%, or +/−5%, and the Mn after 35 days in PBS at 37° C. is from 50%, 55%, 60%, or 65% to 70%, 75%, or 80% of the initial Mn.

In an embodiment, a drug delivery device comprises the random copolymer and a bioactive agent. In an embodiment, the drug delivery device provides for a controlled and/or extended release of a bioactive agent. A drug delivery device may be a pharmaceutical product or a medical device. A pharmaceutical product is a medical product that is administered to a patient and achieves its primary intended purpose through pharmacological action. A medical device is a medical instrument, apparatus, implement, machine, contrivance, implant, in vitro reagent, or other similar or related article, including a component part or accessary thereof, that does not achieve its primary intended purpose through pharmacological action.

In an embodiment, the bioactive agent comprises a nutrient, a pharmaceutical, a small molecule drug, a protein, a peptide, a vaccine, a genetic material, (such as polynucleotides, oligonucleotides, plasmids, DNA and RNA), a diagnostic agent, or an imaging agent. Bioactive agents may be drugs, prodrugs or co-drugs thereof, metabolites thereof, and/or prodrugs of the metabolites.

In an embodiment, the bioactive agent is capable of stimulating or suppressing a biological response. In an embodiment, the bioactive agent is chosen from one or more of growth factors (VEGF, FGF, MCP-1, PIGF, antibiotics (for instance penicillin's such as B-lactams, chloramphenicol), anti-inflammatory compounds, antithrombogenic compounds, anti-claudication drugs, anti-arrhythmic drugs, anti-atherosclerotic drugs, antihistamines, cancer drugs, vascular drugs, ophthalmic drugs, amino acids, vitamins, hormones, neurotransmitters, neurohormones, enzymes, signaling molecules, anti-viral drugs, and psychoactive medicaments.

The bioactive agents can have antiproliferative or anti-inflammatory properties or can have other properties such as antineoplastic, antiplatelet, anti-coagulant, antifibrin, antithrombotic, antimitotic, antibiotic, antiallergic, or antioxidant properties. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-0-(3-hydroxy)propyl-rapamycin, 40-O-[2-(2-hydroxy)ethoxy]ethyl-rapamycin, and 40-0-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia AND Upjohn, Peapack NJ), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hb/nia platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck AND Co., Inc., Whitehouse Station, NJ), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and nonsteroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck and Co., Inc., Whitehouse Station, NJ). An example of an antiallergic agent is permirolast potassium. Other therapeutic substances or agents which may be appropriate include alpha-interferon, pimecrolimus, imatinib mesylate, midostaurin, and genetically engineered epithelial cells.

Further examples of specific bioactive agents are neurological drugs (amphetamine, methylphenidate), alpha1 adrenoceptor antagonist (prazosin, terazosin, doxazosin, ketenserin, urapidil), alpha2 blockers (arginine, nitroglycerin), hypotensive (clonidine, methyldopa, moxonidine, hydralazine minoxidil), bradykinin, angiotensin receptor blockers (benazepril, captopril, cilazepril, enalapril, fosinopril, lisinopril, perindopril, quinapril, ramipril, trandolapril, zofenopril), angiotensin-1 blockers (candesartan, eprosartan, irbesartan, losartan, telmisartan, valsartan), endopeptidase (omapatrilate), beta2 agonists (acebutolol, atenolol, bisoprolol, celiprolol, esmodol, metoprolol, nebivolol, betaxolol), beta2 blockers (carvedilol, labetalol, oxprenolol, pindolol, propanolol) diuretic actives (chlortalidon, chlorothiazide, epitizide, hydrochlorthiazide, indapamide, amiloride, triamterene), calcium channel blockers (amlodipin, barnidipin, diltiazem, felodipin, isradipin, lacidipin, lercanidipin, nicardipin, nifedipin, nimodipin, nitrendipin, verapamil), anti arthymic active (amiodarone, solatol, diclofenac, flecainide) or ciprofloxacin, latanoprost, flucloxacillin, rapamycin and analogues and limus derivatives, paclitaxel, taxol, cyclosporine, heparin, corticosteroids (triamcinolone acetonide, dexamethasone, fluocinolone acetonide), anti-angiogenic (iRNA, VEGF antagonists: bevacizumab, ranibizumab, pegaptanib), growth factor, zinc finger transcription factor, triclosan, insulin, salbutamol, oestrogen, norcantharidin, microlidil analogues, prostaglandins, statins, chondroitinase, diketopiperazines, macrocycli compounds, neuregulins, osteopontin, alkaloids, immuno suppressants, antibodies, avidin, biotin, clonazepam.

In an embodiment, the bioactive agent is useful for treating glaucoma, ocular hypertension, wet age-related macular degeneration (AMD), diabetic retinopathy, diabetic macular edema, or other diseases of the eye. In an embodiment, the bioactive agent comprises latanoprost, bimatoprost, or travoprost.

In an embodiment, the bioactive agent comprises a chemotherapeutic, a JAK kinase inhibitors, an antipsychotic, or an antiviral.

In an embodiment, the bioactive agent comprises one or more of Sorafenib, Pazopanib, Axitinib, Regorafenib, Cabozantinib, Lenvatinib, Sunitinib, Nintedanib, Crizotinib, Ceritinib, Alectinib, Brigatinib, Bosutinib, Dasatinib, Imatinib, Nilotinib, Ponatinib, Vemurafenib, Dabrafenib, Ibrutinib, Palbociclib, Ribociclib, Gefitinib, Erlotinib, Lapatinib, Afatinib, Osimertinib, or Trametinib.

In an embodiment, the bioactive agent comprises one or more of Tofacitinib, Ruxolitinib, Oclacitinib, Baricitinib, Peficitinib, Fedratinib, Upadacitinib, Filgotinib, Cerdulatinib, Gandotinib, Lestaurtinib, Momelotinib, or Pacritinib.

In an embodiment, the bioactive agent comprises one or more of Aripiprazole, Brexpiprazole, Olanzapine, Quetiapine, or Ziprasidone.

In an embodiment, the bioactive agent comprises one or more of Tenofovir, Emtricitabine, Efavirenz, Elvitegravir, Cobicistat, Ribavirin, Daclatasvir, Sofosbuvir, Velpatasvir, Voxilaprevir, Glecaprevir, Pibrentasvir, Elbasvir, Grazoprevir, Simeprevir, or Ledipasvir.

The drug delivery device may take various forms. In an embodiment, the drug delivery device comprises the random copolymer molded into a certain shape. In an embodiment, the drug delivery device comprises the random copolymer coated onto a substrate, such as the surface of a stent. In an embodiment, the drug delivery device comprises an injectable formulation comprising the random copolymer, such as in a solution comprising microparticles or nanoparticles that comprise the random copolymer and the bioactive agent. In an embodiment, the drug delivery device is in the shape of a cylinder, a disc, a spheroid, or a coating, or a plurality of cylinders, discs, spheroid, or coatings.

In an embodiment, the drug delivery device is in the shape of a cylinder having a diameter of from 100, 150, 200, or 250 micrometers to 1000, 900, 800, 700, 600, or 500 micrometers. In an embodiment, the drug delivery device is in the shape of a cylinder having a length of from 0.5, 1, 1.5, 2, 2.5, 3, 3.5, 4, 4.5 or 5 millimeters to 30, 25, 20, 15, 10, 5, 4, or 3 millimeters.

In an embodiment, the drug delivery device is in the shape of a cylinder having a diameter of from 1, 2, 3, 4, or 5 to 4, 5, 6, 7, 8, 9, or 10 mm. In an embodiment, the drug delivery device is in the shape of a cylinder having a length of from 10, 15, 20, 25, or 30 mm to 150, 120, 100, or 80 mm. In an embodiment, the drug delivery device is in the shape of a cylinder having a diameter of 1 to 5 mm and a length of from 20 to 100 mm.

In an embodiment, the drug delivery device comprises a core comprising the random copolymer and a bioactive agent, and a shell comprising a shell polymer. In an embodiment, both the core and the shell comprise a bioactive agent. In an embodiment, only the core comprises a bioactive agent. In an embodiment the core and the shell comprise the same polymer.

In an embodiment, the core and the shell comprise different polymers. In an embodiment, the shell polymer comprises poly(lactic acid), poly(glycolic acid), poly(lactide-co-glycolide), polycaprolactone, or a combination thereof. In an embodiment, the core and the shell each comprise a random polymer according to Formula I.

The core-shell arrangement can take various forms, such as in a coating comprising an inner core layer that is more proximate the substrate than the shell layer. Other layers may be present more proximate the substrate than the core layer, between the core and the shell layer, or more distal than the shell layer.

In an embodiment, the drug delivery device is in the shape of a cylinder and comprises a cylindrical core at least partially surrounded by a cylindrical shell. The shell may surround the entirety of the cylindrical core, may surround only one end of the cylindrical core, or more surround neither end of the cylindrical core.

In embodiment, the drug delivery device is an injectable formulation comprises a plurality of micro- and/or nano-particles comprising the random copolymer and a bioactive agent. In an embodiment, the micro- and/or nano-particles comprise a core comprising the random copolymer and a bioactive agent and a shell surrounding the core.

In an embodiment, an injectable formulation comprises a plurality of micro-particles comprising the random copolymer and a bioactive agent and having a mean particle diameter of from 10 to 500 micrometers. In an embodiment an injectable formulation comprises a plurality of micro-particles comprising the random copolymer and a bioactive agent and having a mean particle diameter of from 10, 20, 30, 40, 50, 60, 70, 80, 90, or 100 micrometers to 500, 475, 450, 425, 400, 375, 350, 325, or 300 micrometers. In an embodiment an injectable formulation comprises a plurality of nano-particles comprising the random copolymer and a bioactive agent and having a mean particle diameter of from 50, 100, 150, 200, 250, 300, 350, 400, 450, or 500 nanometers to 1000, 950, 900, 850, or 800 nanometers. Mean particle diameter is measured by laser diffraction using a Malvern Mastersizer 2000.

In an embodiment, the drug delivery device further comprises another polymer other than the random copolymer of Formula I. Examples of such biocompatible polymers are poly(ortho esters), poly(anhydrides), poly(D,L-lactic acid), poly (L-lactic acid), poly(glycolic acid), copolymers of poly(lactic) and glycolic acid, poly(L-lactide), poly(D,L-lactide), poly(glycolide), poly(D,L-lactide-co-glycolide), poly(L-lactide-co-glycolide), poly(phospho esters), poly(t-rimethylene carbonate), poly(oxa-esters), poly(oxa-amides), poly(ethylene carbonate), poly(propylene carbonate), poly (phosphoesters), poly(phosphazenes), poly(tyrosine derived carbonates), poly(tyrosine derived arylates), poly(tyrosine derived iminocarbonates), copolymers of these polymers with poly(ethylene glycol) (PEG), or combinations thereof. These further polymers may be present along with the random copolymer of Formula I as a blend or may form part or all of another layer or portion of the drug delivery device.

In an embodiment, the drug delivery device comprises a fiber. The fiber may be manufactured via an extrusion process, for example melt extrusion in which the biodegradable polymer and additional compounds are homogenized using a Retsch cryomill. The resulting powder is then filled into a pre-heated DSM Xplore micro-extruder with 5 cc barrel size and twin-screws which are connected to a micro fiber spin device. The biodegradable polymer preferably has a residence time of 5-10 min at 120° C.-140° C. before it is stretched into a fiber with diameter in the range of 100-250 μm. The extrusion is normally performed under inert atmosphere in order to minimize the oxidative degradation of the polymer during the process. Under tension it is subsequently cooled at room temperature. The obtained fiber may then be cut into pieces, for example 4 mm in length, and may be sterilized via gamma radiation.

Alternatively, such fibers can be prepared via injection molding. In this process fibers are formed in an injection molding apparatus at a temperature of 50-200° C., preferably between 100-200° C., resulting in fibers with a diameter of approximately 200 μm. Then the mold may be cooled to room temperature before opening and the fibers removed.

In case that the drug delivery device comprises one or more bioactive agents, the loading of bioactive agent may be achieved by forming the drug delivery device into the desired shape in the presence of the bioactive agent or thereafter. In the case that the bioactive agent is sensitive to the process for forming the drug delivery device into its desired shape, the bioactive agent may be loaded after forming the drug delivery device into its desired shape. This can be achieved by contacting the drug delivery device with the bioactive agent and allowing the bioactive agent to diffuse into the drug delivery device and/or adhere or adsorb to the surface thereof.

The drug delivery devices comprising the random copolymers may be used in the medical field especially in drug delivery in the field of management of pain, MSK, ophthalmology, cancer treatment, vaccine delivery compositions, dermatology, cardiovascular field and orthopedics, spinal, intestinal, pulmonary, nasal, or auricular field.

The Examples below further elucidate embodiments of the invention, but of course, should not be construed as in any way limiting the scope of the claims.

EXAMPLES

Measurement Methods

Wet Tg

Samples are soaked for 4 days in Dulbecco PBS buffer solution at 37° C. Generally, the samples float on top of the buffer solution during about the first three days and are then become saturated enough that they sink into the buffer solution for about the last 24 hours of the soaking process.

A schematic of the modified geometry of the test setup is shown in FIG. 1. The measurements are performed on an ARES2-rheometer. A sample 1 is placed between 15 mm diameter parallel plates 2. The ARES2-rheometer is modified to contain PBS buffer 3 to create a saturated atmosphere.

The temperature ramp is 70° C. to 0° C. at a cooling rate of 5° C./min, an angular frequency of 1 Hz (6.28 rad/s), and a variable strain (autostrain control enabled) with an initial value of 0.1%. The gap is controlled manually to ensure a constant axial force (compression) on the sample ($F_N$~30 grams). This constant compressive force is necessary to prevent a loss of contact between the sample and the parallel plates.

Dry Tg

Figure 2:
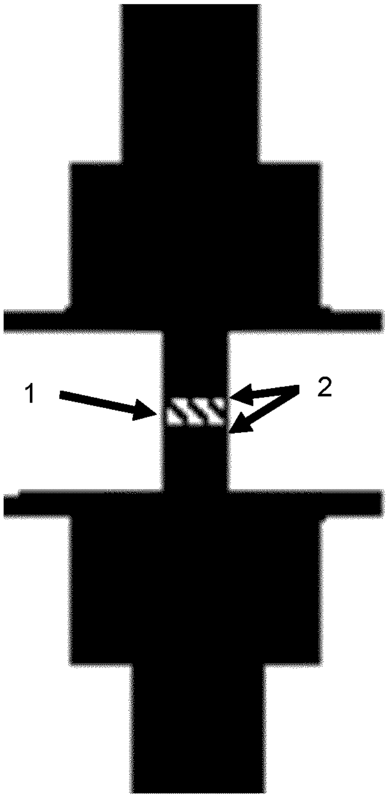
FIG. 2 is a schematic of a dry Tg test apparatus.

A schematic of the test setup is shown in FIG. 2. The measurements are performed on an ARES2-rheometer. The parallel plates 2 are approximately the same dimensions as the test sample 1, in this case, 4 mm in diameter. The measurements are conducted in an $N_2$ atmosphere.

Samples are dried for 7 days at 25° C. under 200 mbar nitrogen atmosphere. The temperature ramp is 90° C. to 0° C. (cooling rate @ 5° C./min) at an angular frequency of 1 Hz (6.28 rad/s) and a variable strain (autostrain control enabled) with an initial value of 0.1%. The gap is controlled manually to ensure a constant axial force (compression) on the sample ($F_N$~30 grams). This constant compressive force is necessary to prevent a loss of contact between the sample and the parallel plates.

Molecular Weight

Mn is measured via GPC using THF as the mobile phase on dried samples. Molecular weights are relative to polystyrene standards.

Preparation of Copolymers Used in the Examples

Test samples are made according to the following procedures.

Figure 3:
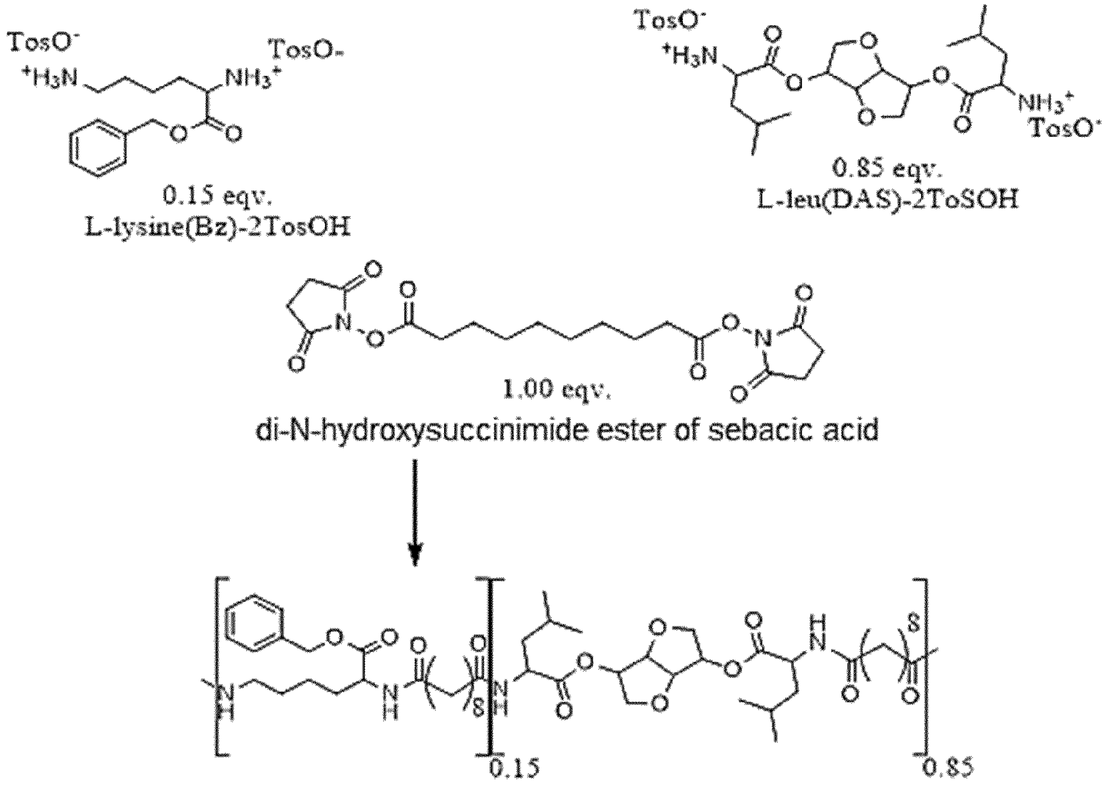
FIG. 3 is a reaction scheme for forming a random copolymer according to Formula VI.

The random copolymer according to Formula VI is prepared by the following procedure. Triethylamine (30 mL, 0.215 mole) and DMSO (52 mL, 0.732 mole) are added to a mixture of di-N-hydroxysuccinimide ester of sebacic acid (Di-NHS-sebacic acid) (38.541 g, 0.097 mole), L-leucine-(DAS)-2TosOH (59.244 g, 0.083 mole) and L-lysine(Bz)-2TosOH (8.469 g, 0.014 mole) in a nitrogen flushed 500 mL round bottomed flask equipped with an overhead stirrer at room temperature. The subsequent mixture is heated to 60° C. to allow the reaction to proceed and monitored by GPC analysis in THF. After 36 hours a stable molecular weight is obtained. The mixture is allowed to cool to room temperature. At room temperature acetic anhydride (1.89 mL, 0.0199 mole) is added to acylate the amino functional end groups of the polymer. The mixture was stirred at room temperature for 24 hours. The general reaction scheme is shown in FIG. 3.

The obtained crude polymer mixture is precipitated in water at a 10:1 ratio (water:reaction mixture). The polymer is collected and dissolved in ethanol (500 mL, 8.57 mole) and then precipitated a second time. The polymer is again dissolved in ethanol (500 mL, 8.57 mole) and precipitated in ethylacetate (5000 mL, 50.91 mole) by drop wise addition to a stirring solution. The precipitated polymer is washed with ethylacetate (100 mL, 1.00 mole), the supernatant is removed, and the precipitate is washed again in ethylacetate again (100 mL, 1.00 mole). After the removal of the supernatant, the precipitate is dried and dissolved in ethanol (500 mL, 8.57 mole), and filtered over a 0.2 μm PTFE membrane filter. The filtered polymer solution is dried under reduced pressure at 65° C. Yield 75%, Mn=108 kDa (Gel Permeation Chromatography (GPC) in THF relative to polystyrene standards).

The random copolymer according to Formula VII is prepared by the following procedure. Triethylamine (30 mL, 0.215 mole) and DMSO (52 mL, 0.732 mole) are added to a mixture of di-N-hydroxysuccinimide ester of sebacic acid (Di-NHS-sebacic acid) (38.541 g, 0.097 mole), L-leucine-(DAS)-2TosOH (59.244 g, 0.083 mole), L-lysine·2HCl (1.598 g, 0.007 mole) and L-lysine(Bz)-2TosOH (4.235 g, 0.007 mole) in a nitrogen flushed 500 mL round bottomed flask equipped with an overhead stirrer at room temperature. The subsequent mixture is heated to 60° C. to allow the reaction to proceed and monitored by GPC analysis in THF. After 36 hours a stable molecular weight is obtained. The mixture is allowed to cool to room temperature. At room temperature acetic anhydride (1.89 mL, 0.0199 mole) is added to acylate the amino functional end groups of the polymer. The mixture was stirred at room temperature for 24 hours.

The obtained crude polymer mixture is precipitated in water at a 10:1 ratio (water:reaction mixture). The polymer is collected and dissolved in ethanol (500 mL, 8.57 mole) and then precipitated a second time. The polymer is again dissolved in ethanol (500 mL, 8.57 mole) and precipitated in ethylacetate (5000 mL, 50.91 mole) by drop wise addition to a stirring solution. The precipitated polymer is washed with ethylacetate (100 mL, 1.00 mole), the supernatant is removed, and the precipitate is washed again with ethylacetate (100 mL, 1.00 mole). After the removal of the supernatant, the precipitate is dried and dissolved in ethanol (500 mL, 8.57 mole), and filtered over a 0.2 μm PTFE membrane filter. The filtered polymer solution is dried under reduced pressure at 65° C. Yield 75%, Mn=62 kDa (Gel Permeation Chromatography (GPC) in THF relative to polystyrene standards).

Figure 4:
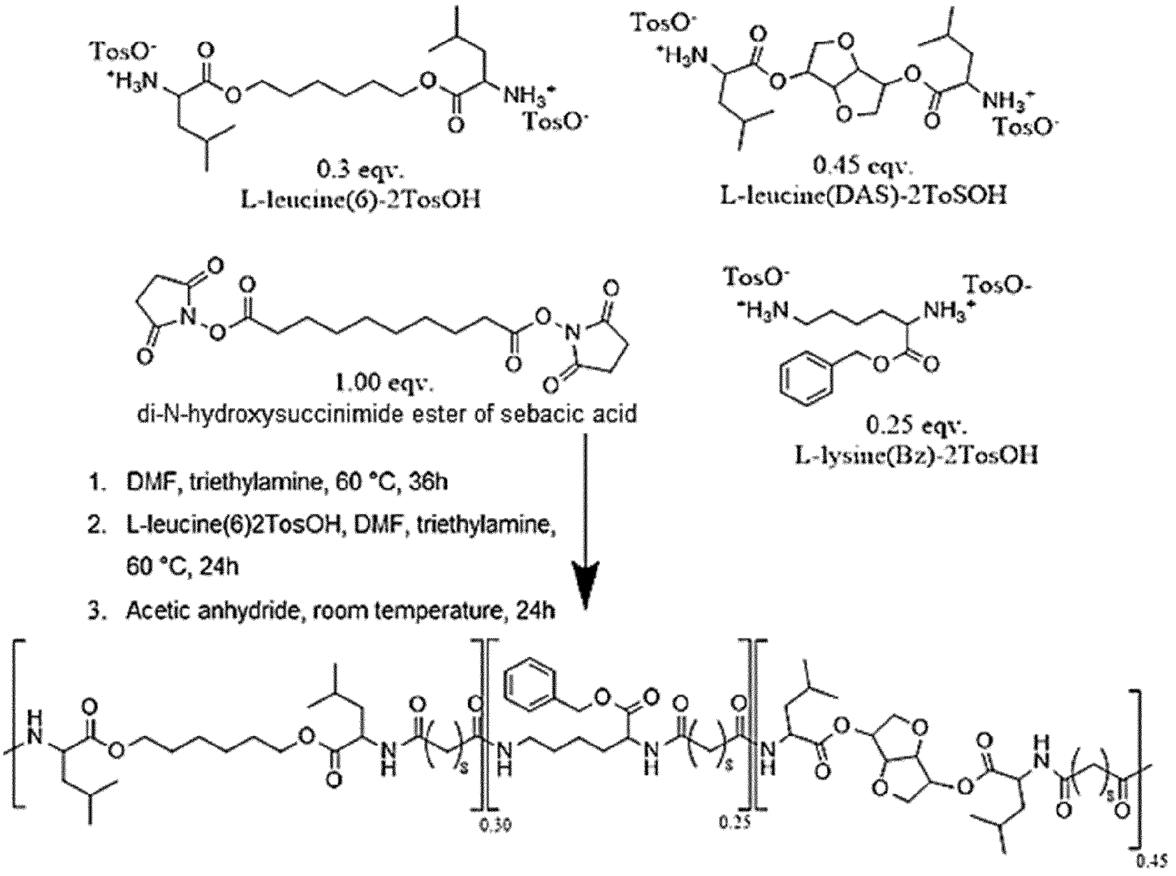
FIG. 4 is a reaction scheme for forming PEA III AcBz.

PEA III AcBz according to Formula VIII is obtained as follows. Triethylamine (30.9 mL, 0.222 mole, 2.2 eq) and N,N-dimethylformamide (53.07 mL, 0.689 mole) are added to a mixture of di-N-hydroxysuccinimide ester of sebacic acid (Di-NHS-sebacic acid) (39.940 g, 0.1008 mole, 1.0 eq), L-leucine(6)-2TosOH (20.823 g, 0.0302 mole, 0.30 eq), L-leucine-(DAS)-2TosOH (32.503 g, 0.0453 mole, 0.45 eq) and L-lysine(Bz)-2TosOH (14.628 g, 0.0252 mole, 0.25 eq) in a nitrogen flushed 500 mL round bottomed flask equipped with an overhead stirrer at room temperature. The subsequent mixture is heated to 60° C. to allow the reaction to proceed and monitored by GPC analysis in THF. After 36 hours a stable molecular weight is obtained, subsequently a portion of L-leucine(6)-2TosOH (4.338 g, 0.0063 mole) along with triethylamine (1.76 mL, 0.0126 mole) and N,N-dimethylformamide (4.54 mL, 0.0590 mole) was added to terminate the polymerization reaction. The mixture is heated additionally for 24 hours after which the viscous solution was further diluted with N,N-dimethylformamide (407.85 g, 5.301 mole) and allowed to cool to room temperature. At room temperature acetic anhydride (1.89 mL, 0.0199 mole) is added to acylate the amino functional end groups of the polymer. The mixture was stirred at room temperature for 24 hours. The general reaction scheme is shown in FIG. 4.

The obtained crude polymer mixture is precipitated in water at a 10:1 ratio (water: reaction mixture). The polymer is collected and dissolved in ethanol (500 mL, 8.57 mole) and then precipitated a second time. The polymer is again dissolved in ethanol (500 mL, 8.57 mole) and precipitated in ethylacetate (5000 mL, 50.91 mole) by drop wise addition to a stirring solution. The precipitated polymer is washed with ethylacetate (100 mL, 1.00 mole), the ethylacetate removed, and then the polymer is washed in ethylacetate again (100 mL, 1.00 mole). The polymer is then dried and dissolved in ethanol (500 mL, 8.57 mole) and filtered over a 0.2 μm PTFE membrane filter. The filtered polymer solution is dried under reduced pressure at 65° C. Yield 75%, Mn=43.3 kDa (Gel Permeation Chromatography (GPC) in THF relative to polystyrene standards.

PEA III X25 according to Formula IX may be obtained as follows. Triethylamine (31 mL, 0.222 mole) and DMSO (54 mL, 0.76 mole) are added to a mixture of di-N-hydroxysuccinimide ester of sebacic acid (Di-NHS-sebacic acid) (39.336 g, 0.099 mole), L-leucine-(DAS)-2TosOH (32.876 g, 0.045 mole), L-leucine(6)-2TosOH (21.062 g, 0.030 mole), L-lysine·2HCl (1.396 g, 0.006 mole) and L-lysine (Bz)-2TosOH (4.235 g, 0.018 mole) in a nitrogen flushed 500 mL round bottomed flask equipped with an overhead stirrer at room temperature. The subsequent mixture is heated to 60° C. to allow the reaction to proceed and monitored by GPC analysis in THF. After 36 hours a stable molecular weight is obtained. The reaction mixture is diluted with 250 mL DMSO and is allowed to cool to room temperature. At room temperature acetic anhydride (1.89 mL, 0.0199 mole) is added to acylate the amino functional end groups of the polymer. Next, the mixture is stirred at room temperature for 24 hours.

The obtained crude polymer mixture is precipitated in water at a 10:1 ratio (water: reaction mixture). The polymer is collected and dissolved in ethanol (500 mL, 8.57 mole) and then precipitated a second time. The polymer is again dissolved in ethanol (500 mL, 8.57 mole) and precipitated in ethylacetate (5000 mL, 50.91 mole) by drop wise addition to a stirring solution. The precipitated polymer is washed with ethylacetate (100 mL, 1.00 mole), the supernatant is removed, and the precipitate is washed again with ethylacetate (100 mL, 1.00 mole). After the removal of the supernatant, the precipitate is dried and dissolved in ethanol (500 mL, 8.57 mole), and filtered over a 0.2 μm PTFE membrane filter. The filtered polymer solution is dried under reduced pressure at 65° C. The typical yield is 75%, Mn is typically in the range of 45-70 kDa (Gel Permeation Chromatography (GPC) in THF relative to polystyrene standards).

The copolymers formed are listed in the below Table 0.1. For each copolymer according to Formula I, $R^1$ is $-(CH_2)_8-$, $R^4$ is $(CH_3)_2CH-CH_2-$; $R^5$ is $-(CH_2)_6-$, $R^6$ is according to Formula II; $R^7$ is $C_6$aryl-$CH_2-$, and $R^8$ is $-(CH_2)_4-$.

TABLE 0.1

Copolymers Used in the Examples

| Name | Formula | m | n | q |
|---|---|---|---|---|
| PEA 100D | I | 0 | 1 | 0 |
| PEA 85D15L | I and VI | 0.15 | 0.85 | 0 |
| PEA 85D15L X50 | I and VII | 0.075 | 0.85 | 0.075 |
| PEA 85D15L X25 | I | 0.112 | 0.85 | 0.038 |
| PEA 65D35L | I | 0.35 | 0.65 | 0 |
| PEA 50D50L | I | 0.50 | 0.50 | 0 |
| PEA III AcBz | VIII | N/A | N/A | N/A |
| PEA III X25 | IX | N/A | N/A | N/A |

PEA 85D15L is according to Formula VI.
Formula VI
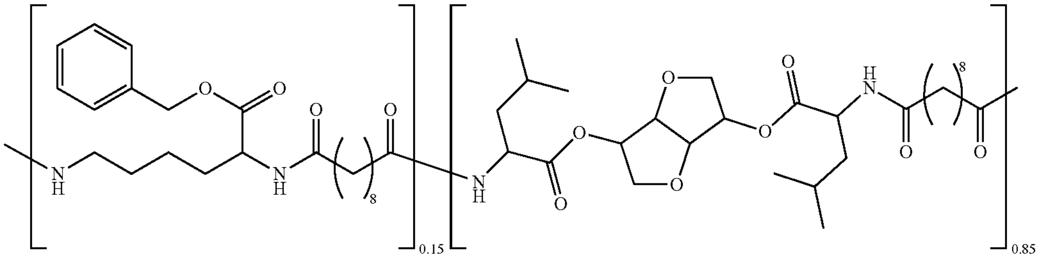
PEA 85D15L X50 is according to Formula VII.
Formula VII
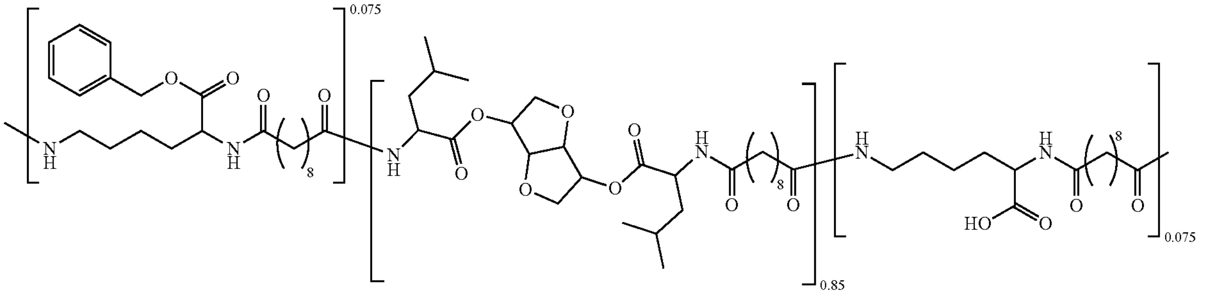
PEA III AcBz is a random copolymer according to Formula VIII.
Formula VIII
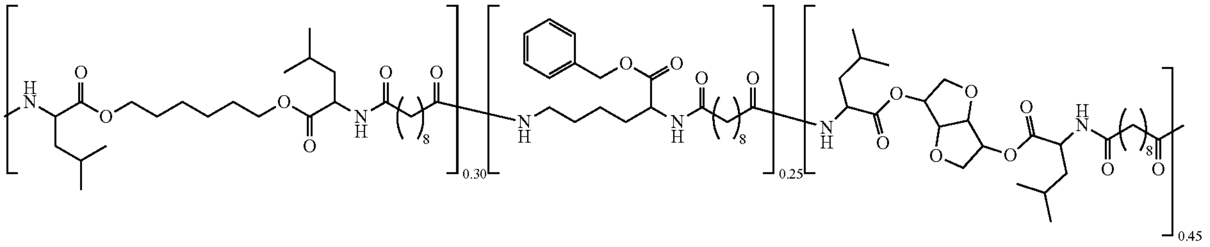
PEA III X25 is a random copolymer according to Formula IX.
Formula IX
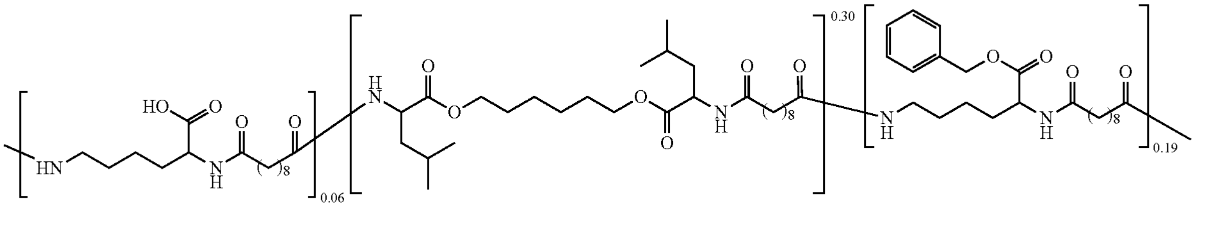

-continued

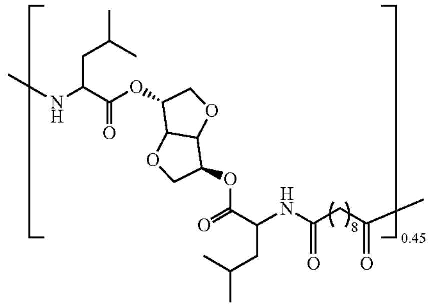

Example 1—Tg

The polymers are compression molded into disc shaped samples having a diameter of 25 mm and a thickness of 0.5 mm using a Fontijne TP200 table press. The press chamber is constantly flushed with $N_2$ gas during molding. Sheets of Teflon™ foil are placed on the mold surfaces to prevent adhesion of the materials to the mold surfaces. The molding is carried out according to the procedure in Table 1.1:

TABLE 1.1

| Disc Compression molding Procedure | | | |
|---|---|---|---|
| Step | Time (min) | Temperature (° C.) | Pressure (kN) |
| 1 | 6 | 120 | 0 |
| 2 | 3 | 120 | 50 |
| 3 | 10 | Cooling to sample temperature of 25° C. | 180 |

Smaller disks having a diameter of 4 mm and a thickness of 0.5 mm are then punched from the larger 25 mm diameter discs. Initial Dry Tg, Initial Wet Tg, and Initial Mn are measured. The results are shown in Table 1.2.

TABLE 1.2

| Initial Mn, Initial Dry Tg, and Initial Wet Tg | | | |
|---|---|---|---|
| Polymer | Mn (kDa) | Dry Tg (° C.) | Wet Tg (° C.) |
| PEA III AcBz | 43.3 | 62 | 21 |
| PEA 50D50L | 45.3 | 68 | 24 |
| PEA 65D35L | 46.1 | 77 | 31 |
| PEA 85D15L | 108.2 | 90 | 39 |
| PEA 85D15L X50 | 62.1 | 88 | 39 |
| PEA 100D | 70.9 | 93 | 43 |

Figure 5:
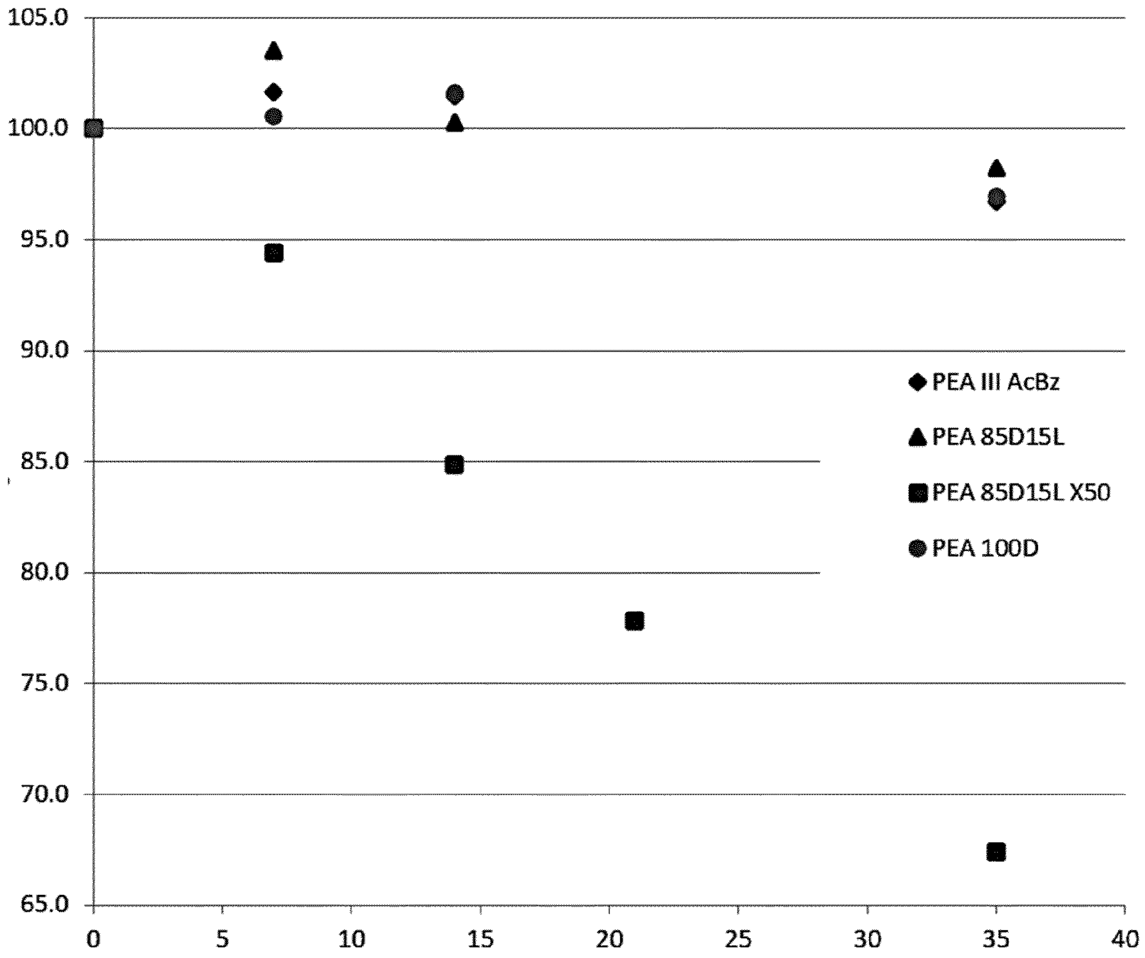
FIG. 5 is a graph of Mn as a percentage of initial Mn vs. days associated with Example 1.

Samples of PEA III AcBz, PEA 85D15L, PEA 85D15L X50, and PEA 1000 are placed in a PBS buffer at 37° C. Wet Tg and Mn are measured at specified time periods over the course of 35 days. Results of the Wet Tg measurements over time is shown in Table 1.3. Mn (kDa) (as a percentage of initial Mn) over time is plotted in FIG. 5.

TABLE 1.3

| Wet Tg Over Time | | | | |
|---|---|---|---|---|
| Time (days) | PEA III Ac Bz Wet Tg (° C.) | PEA 85D15L Wet Tg (° C.) | PEA85D15L X50 Wet Tg (° C.) | PEA100D Wet Tg (° C.) |
| 0 | 21 | 39 | 39 | 43 |
| 3 | 21 | 39 | 39 | 43 |
| 7 | 21 | 39 | 39 | 44 |
| 14 | 21 | 37 | 35 | 45 |
| 21 | | | 35 | |
| 35 | 21 | 40 | 37 | 47 |

The Wet Tg stays approximately constant during the tested time period. The expected reason for the Mn decrease of 85D15L X50 is the hydrolysis of the unprotected carboxylic acid groups, which are not present in the other copolymers. Surprisingly, Mn decrease does not affect the stability of the Wet Tg. This Wet Tg stability and degradation profile is expected to be useful for long term drug delivery applications.

Example 2—In Vitro Release

Cylindrical implants are formed by injection molding. First, a powder is prepared as follows. A formulation of polymer and bioactive agent dissolved in ethanol at from 1 to 30% solids, depending on the bioactive agent and polymer. The formulation is cast onto a FEP (fluorinated ethylene propylene) plate. The resulting film is dried under vacuum at 37° C. The film is then cryogenically milled to obtain a powder.

The obtained powder is used to injection mold implants according to the follow procedure. A Thermo Fisher Scientific HAAKE MiniJet Pro is outfitted with a custom mold. The molding temperature is from 90 to 130° C. The obtained implants are either a diameter of 250 μm, if the implant is not coated, or 230 μm, if a coating layer is to be added.

In the case that the implant is to be coated, the coating is prepared by dip coating. The implants are clamped in a metal paperclip held by an Ametek CS225 Force tester. The coating solution is a 12.3 wt % solution of polymer in acetone for coating with polyesters or a 15 wt % solution of polymer in ethanol for coating with PEAs. The dipping speed is 1.5 cm/s for coating with polyesters and 0.83 cm/s down, 0.33 cm/s up for coating with PEA.

The implants are trimmed to 2 mm in length. The mass of each implant is about 100 μg.

The loading of bioactive agent is verified by UPLC-UV. Samples are solubilized in ethanol (typically, 1 mL solution for a 100 μg sample), and measured with a Waters UPLC-UV (Ultra Performance Liquid Chromatography) using the following settings.

Eluent: 60% acetonitrile—40% MQ water, 0.01% v/v Trifluoroacetic acid
Flow: 0.4 mL/min
Run time: 4 minutes
Column: Acquity C18 BEH 1.7 μ 2.1*50 mm
Detection wavelength: 210 nm
Injection volume: 10 μL for release samples, 2 μL for loading determinations In vitro release experiments are performed by putting a 2 mm implant in a silanized HPLC vial containing 0.5 to 1.8 mL phosphate buffer. Adsorption behavior of travoprost/latanoprost on glass can be minimized by use of silanized vials and dilution of the release samples as follows. Samples obtained from the release experiment are first diluted by adding acetonitrile to the HPLC vial at 1:1 by volume. The samples are analyzed using UPLC-UV as described above.

Samples are pulled mostly following the scheme: day 1, 2, 3, 4, 7, 9, 11, 14, 17, 21, and then one sampling every week.

Results are presented either as cumulative release in % of the payload and/or as extrapolated daily dose. For extrapolated daily dose, the assumption is made that the release rate is constant over the time period between two samplings.

Example 2a—In Vitro Travoprost Release

Implants are formed as detailed above using the stated polymer. All implants are uncoated. The bioactive agent is travoprost ester (CAS #157283-68-6). Three sets of implants are created:

| Ex. | Polymer | Polymer Mn (kDa) | Travoprost (wt %) |
|---|---|---|---|
| 2a-1 (comp.) | PEA III X25 | 50 | 15 |
| 2a-2 | PEA 85D15L X50 | 69 | 15 |
| 2a-3 | PEA 85D15L X25 | 73 | 15 |

Figure 6:
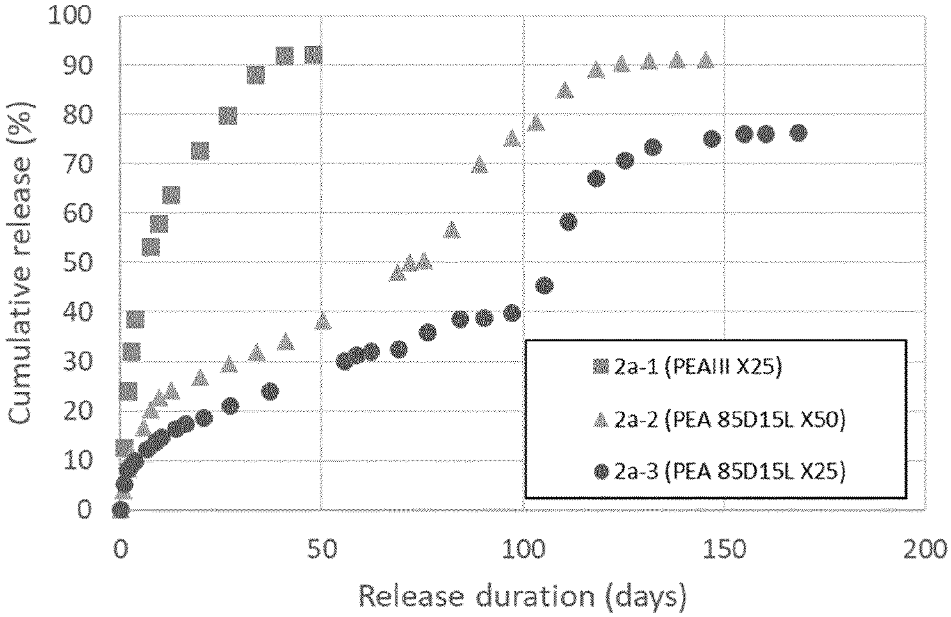
Figure 7:
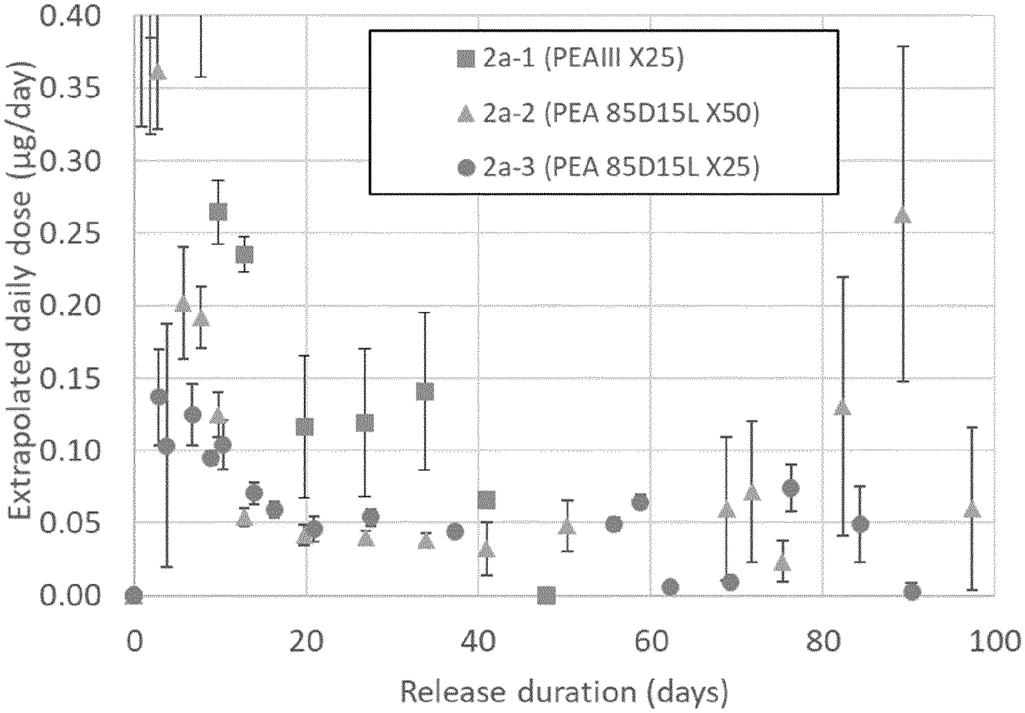
Figure 8:
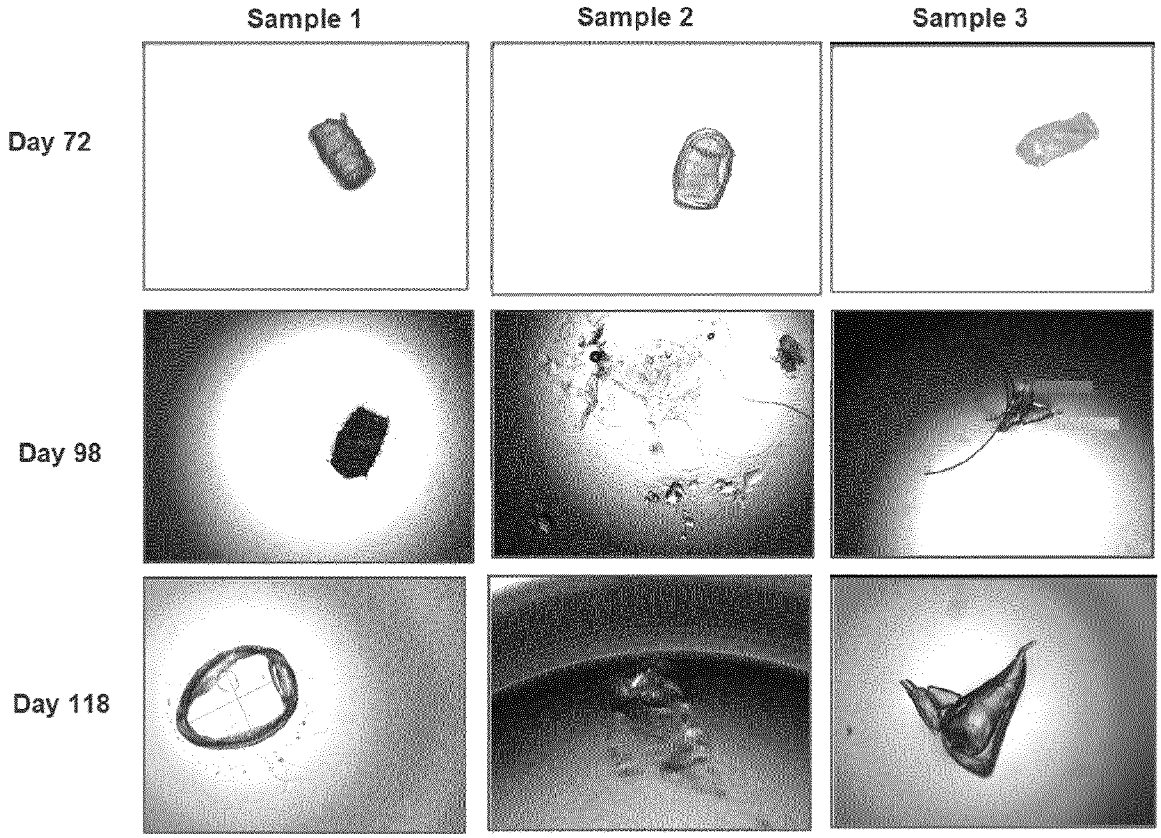
Figure 9:
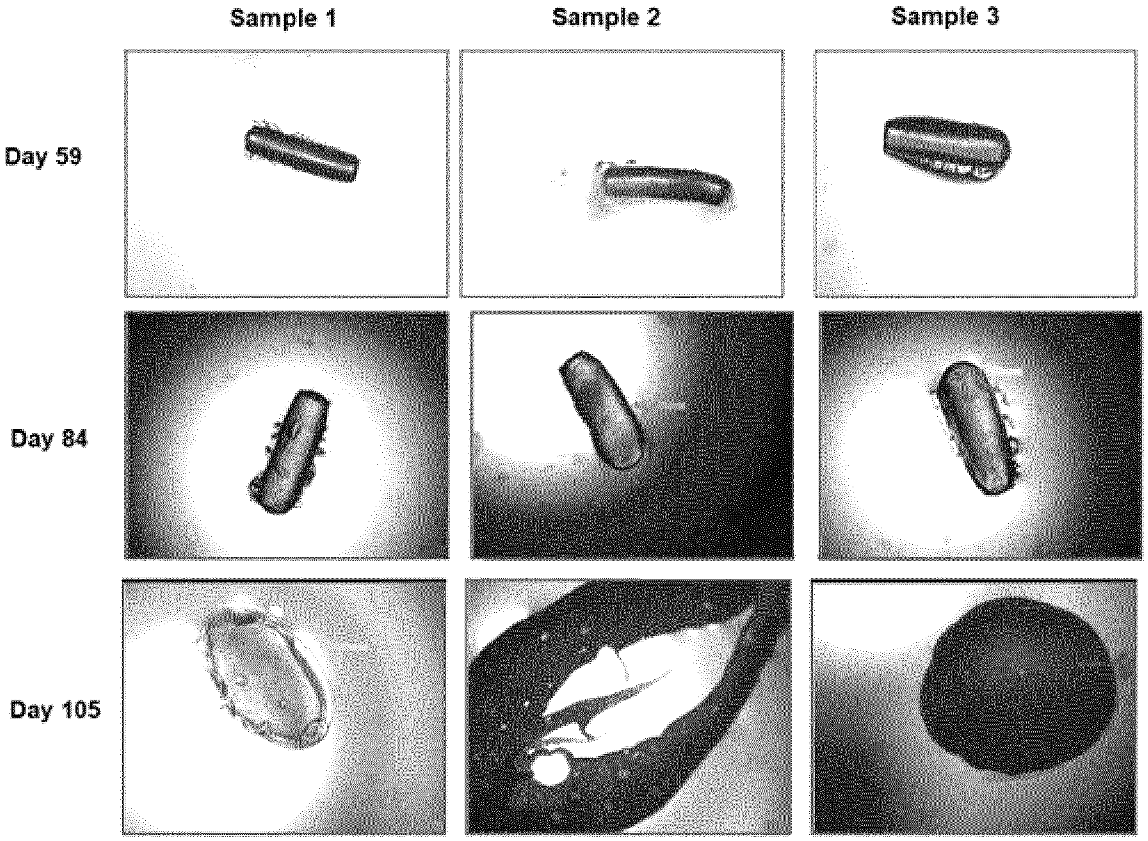

Cumulative release (%) overtime is shown in FIG. 6. Extrapolated daily dose (μg/day) over time is shown FIG. 7. FIGS. 8 and 9 are composites of optical microscopy images at three time periods for 2a-2 and 2a-3, respectively.

Release of travoprost for up to about 130 days is demonstrated. A second burst that leads to rapid release of the remaining travoprost is observed for both of experiments 2a-2 and 2a-3. This second burst seems to correlate with shape change of the implants. See FIGS. 8 and 9 wherein 2a-2 and 2a-3 undergo substantial flattening of the implant at around day 100 that leads to a higher release rate of the remaining travoprost within 30 to 40 days.

Example 2b—Release Kinetics at Different Travoprost Loading

Implants are formed as detailed above using the stated polymer. All implants are uncoated. The bioactive agent is travoprost ester (CAS #157283-68-6). Two sets of implants are created:

| Ex. | Polymer | Polymer Mn (kDa) | Travoprost |
|---|---|---|---|
| 2b-1 | PEA 85D15L X25 | 69 | 10 |
| 2b-2 | PEA 85D15L X25 | 73 | 15 |

Figure 10:
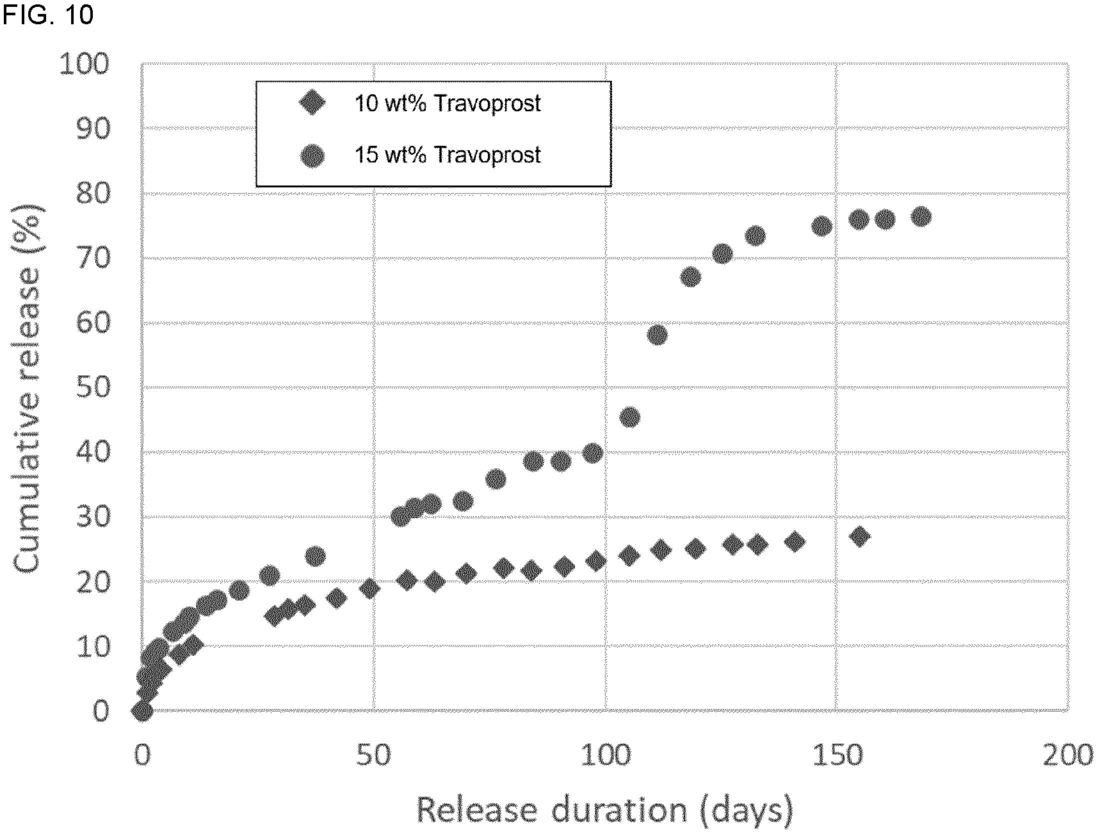
FIG. 10 is a graph of cumulative release overtime associated with Example 2b.
Figure 11:
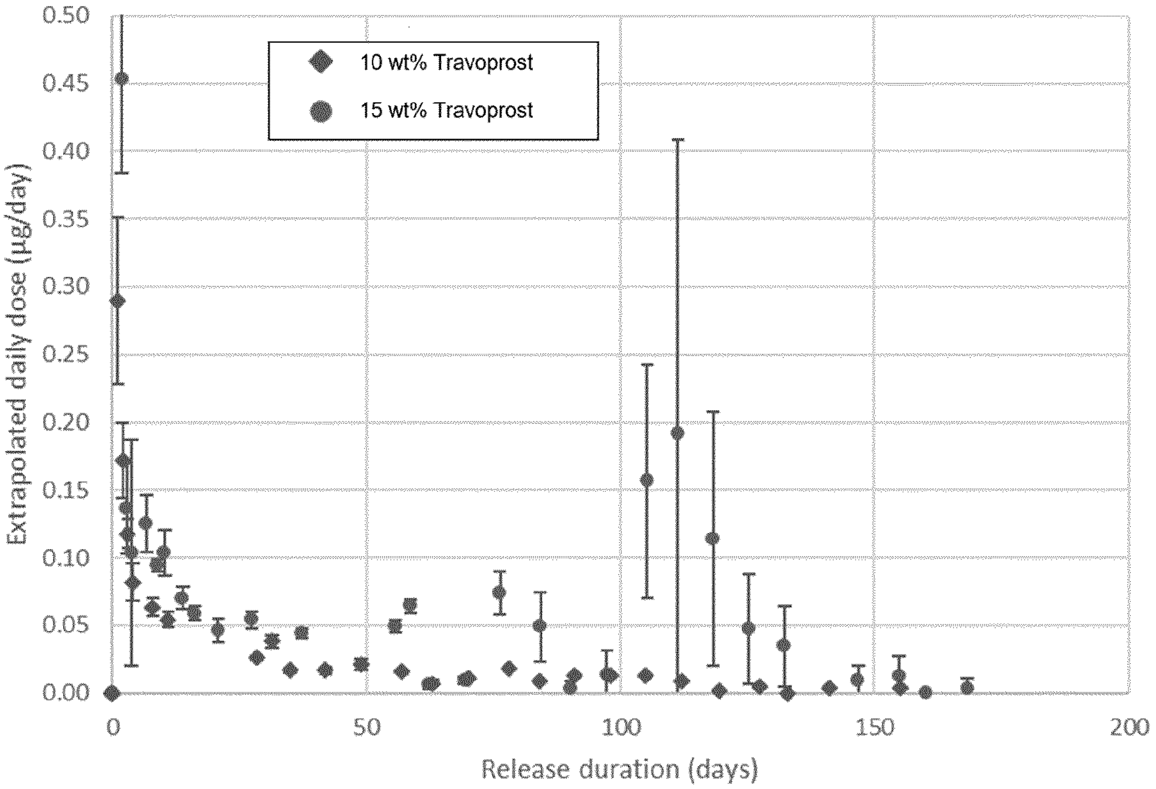
FIG. 11 is a graph of extrapolated daily dose (µg/day) over time associated with Example 2b.
Figure 12:
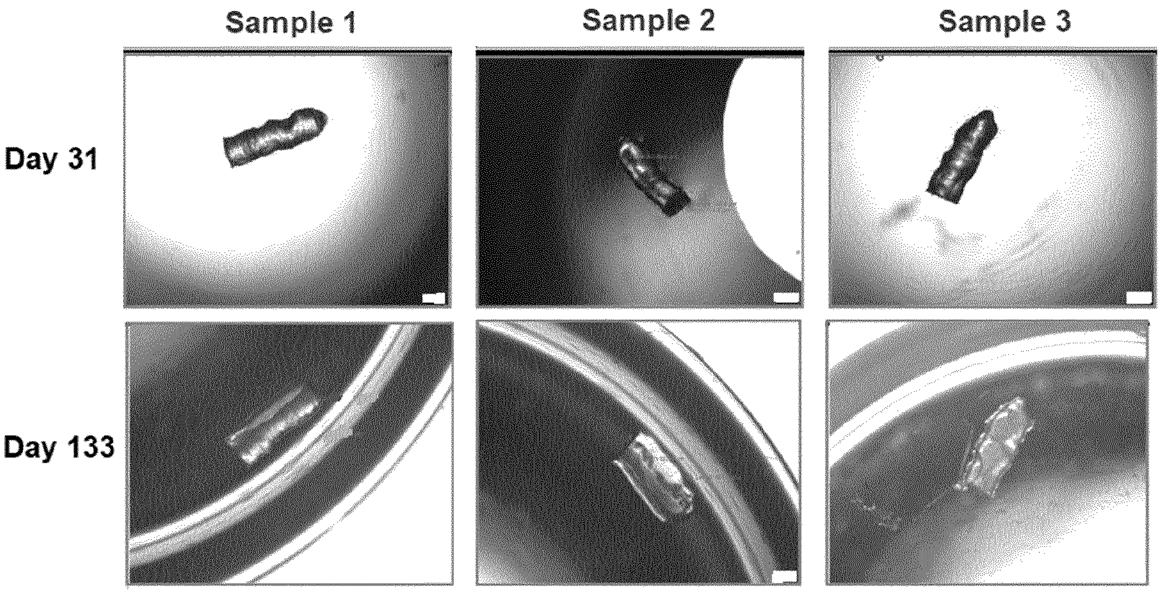
FIG. 12 is a composite of optical microscopy images at two time periods of a PEA85D15L X25 implant (2b-1) associated with Example 2b.

Cumulative release (%) overtime is shown in FIG. 10. Extrapolated daily dose (μg/day) over time is shown FIG. 11. FIG. 12 is a composite of optical microscopy images at Day 31 and Day 133 for samples in set 2b-1.

The release rate in % of total load is lower for the formulation at 10 wt % than for the formulation at 15 wt %. Translated into daily doses, the difference is quite large, and is not directly correlated to the loading of travoprost. The implants loaded at 10 wt % also do not exhibit the second burst as observed for the 15 wt % formulation. It is indeed the case that the 10 wt % implants keep their shape for longer time than the 15 wt % implants; this is illustrated by comparing FIG. 9, where substantial flattening is observed, with FIG. 12, where the implant keeps its shape. The residual concentration of travoprost in the implants at 100 days is about 7.5 wt % for the 15 wt % travoprost implants and about 7 wt % for the 10 wt % travoprost implants. Based on these calculations, no direct link is found between the concentration of travoprost at a certain time late in the polymer degradation process, and the shape change or second burst.

Due to the unexpected low release rate, one implant from the batch at 10 wt % travoprost is extracted at around Day 80 to check mass balance. A residual amount of travoprost matching expectation is recovered from the implant.

Example 2c—In Vitro Latanoprost Release

Implants are formed as detailed above using the stated polymer. Only the PEA III X25 based implant is coated. The coating polymer is PLGA. The bioactive agent is latanoprost (CAS #130209-82-4). Three sets of implants are created:

| Ex. | Polymer Core | Polymer Core Mn (kDa) | Latanoprost in core (wt %) | Coating |
|---|---|---|---|---|
| 2c-1 (comp.) | PEA III X25 | 60 | 15 | PLGA |
| 2c-2 | PEA 85D15L X50 | 69 | 15 | None |
| 2c-3 | PEA 85D15L X25 | 73 | 15 | None |

In this experiment, there is a non-optimal sampling methodology used during the first weeks, leading to possible adsorption of latanoprost on the glass vials. Accordingly, only the release duration can be accurately determined because duration is not influenced by possible loss due to adsorption, in contrast to the daily dose.

Figure 13:
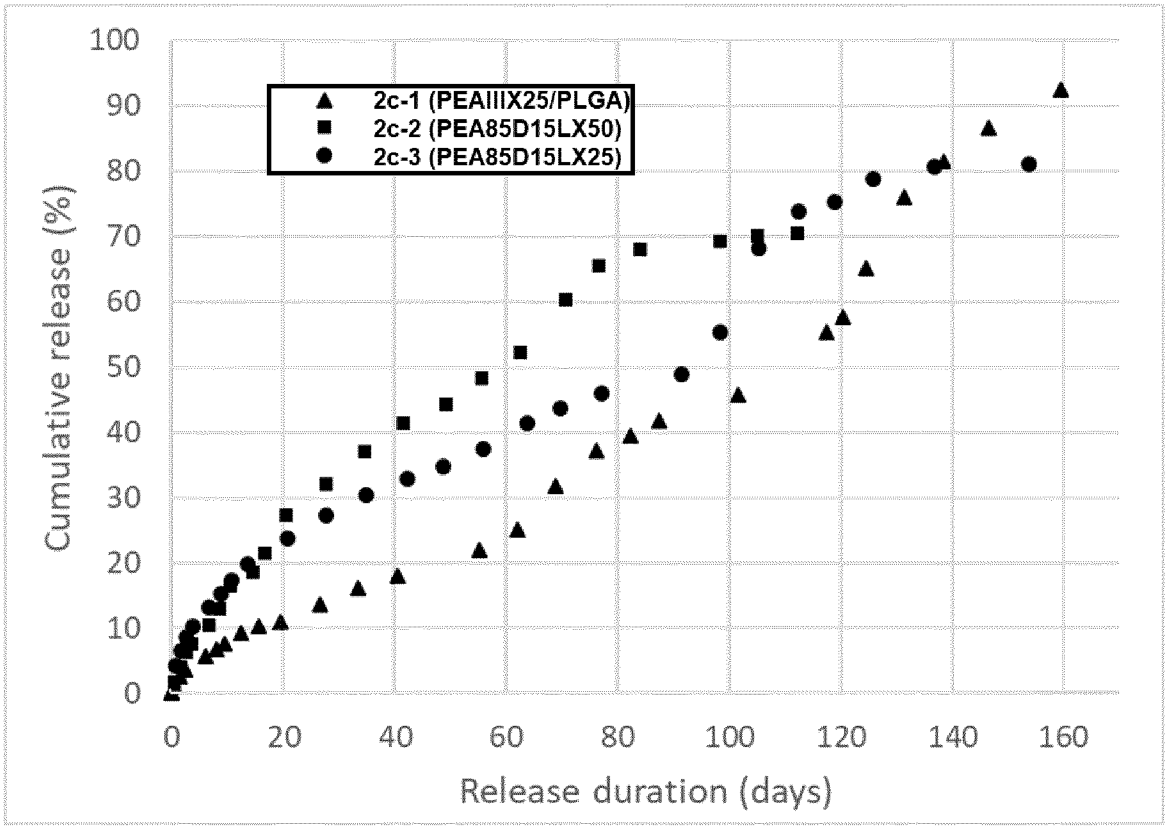
FIG. 13 is a graph of cumulative release overtime associated with Example 2c.
Figure 14:
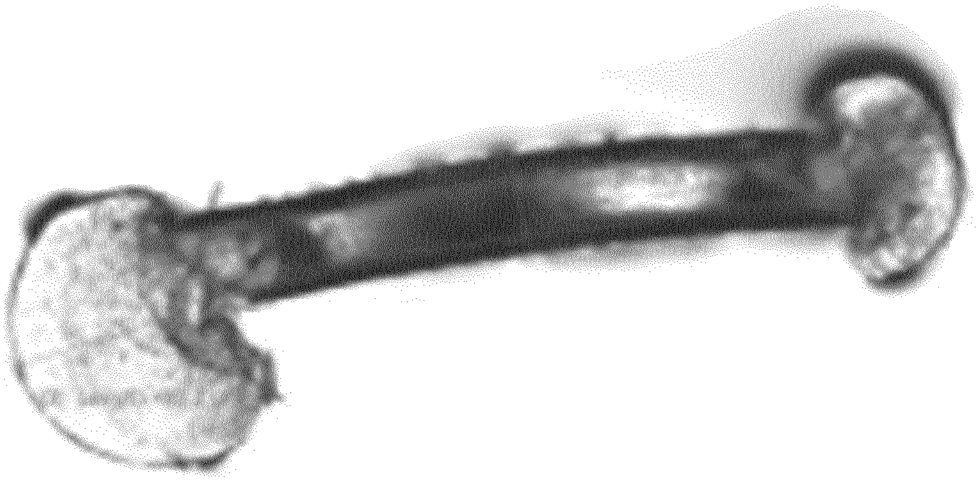
FIG. 14 is an optical microscopy image showing the typical appearance of implants having the composition of Ex. 2c-1 (PEA III X25 core, PLGA shell) after a few weeks of release in phosphate buffer at 37° C.

Cumulative release (%) overtime is shown in FIG. 13. FIG. 14 is an optical microscopy image showing the typical appearance of implants having the composition of 2c-1 after a few weeks in phosphate buffer at 37° C.

Each of 2c-1, 2c-2, and 2c-3 polymer grades allow sustained release of latanoprost for several months. PEA 85D15L X50 shows sustained release for over 2 months and PEA 85D15L X25 for over 3 months. In the case of PEA 85D15L X25 a late burst is observed around 90 days. For PEA 85D15L X50, the implants seem to have released all latanoprost before reaching this time point. These curves do not reach 100% release, which can be explained by possible loss of a part of the latanoprost via adsorption. A coating of PLGA may further increase the release time. However, as shown in FIG. 14, the shape of the implant changes such that plasticized polymer is released from the extremities of the implant. The shape of the implant increases in length during this time. Implants that undergo a shape change in this way may be unsuitable for use in an intracameral application where the limited chamber volume may require an implant to have limited and stable (or decreasing in time) volume.

Example 2d—Effect of Coating of PEA 85D15L on Latanoprost Release

In order to reduce the burst in the first days, the approach of coating implants with a polymer layer containing no bioactive agent is taken. Previous results have shown that coating with polymers such as PLGA or PLA substantially reduce the burst, however it is expected that such a coating will reduce the latanoprost release from PEA 85D15L formulations to a level that will be lower than the desired daily dose. For this reason, an attempt is made to coat the implants with the same polymer as used for the cores.

Implants are formed as detailed above using the stated polymer. The bioactive agent is latanoprost (CAS #130209-82-4). Two sets of implants are created:

| Ex. | Polymer Core | Latanoprost in core (wt %) | Coating |
|---|---|---|---|
| 2d-1 | PEA 85D15L X50 | 15 | None |
| 2d-2 | PEA 85D15L X50 | 15 | PEA 85D15L X50 |

Figure 15:
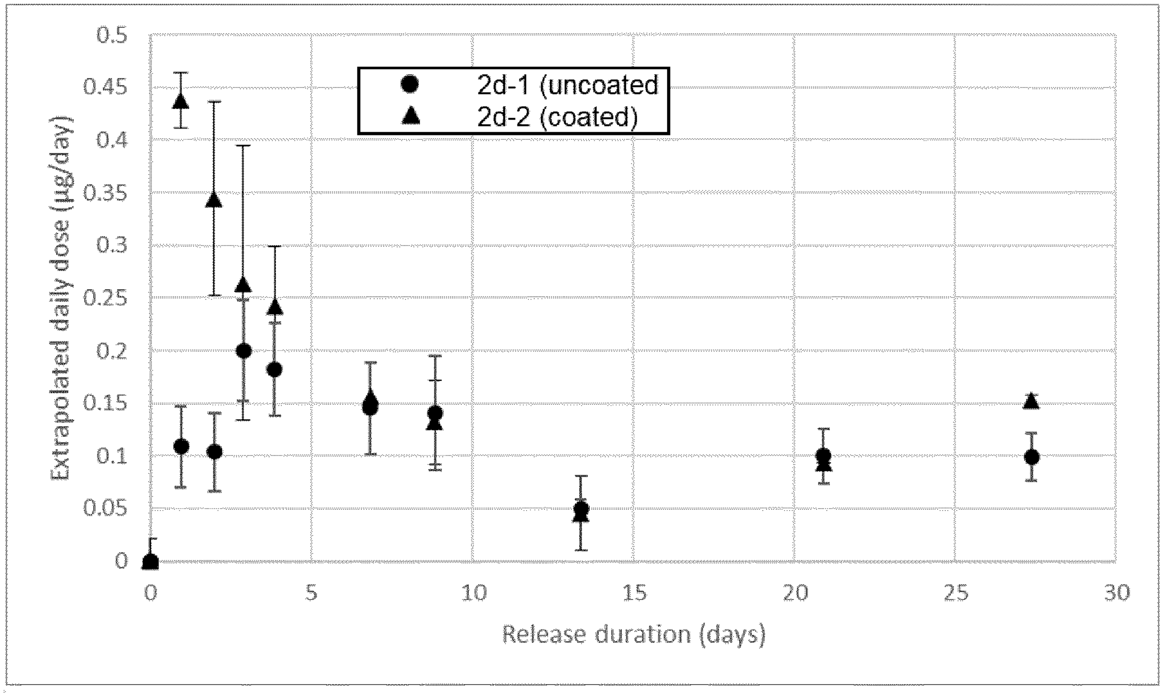
FIG. 15 is a graph of extrapolated daily dose (µg/day) overtime associated with Example 2d.

Extrapolated daily dose (μg/day) over the first 30 days of release is shown in FIG. 15. Lower dose is released in the two first days from the coated implant vs. the uncoated. This is theorized as being due to the fast migration of latanoprost through the polymeric matrix. Because the daily dose for both sets of implants already reaches about the same level at about 6 days, it is expected that the coated and uncoated implants will not have significantly differing release durations. However, the coating may be useful to inhibit burst release.

Additional Description of Exemplary Embodiments

1. A random copolymer according to Formula I:

Formula I

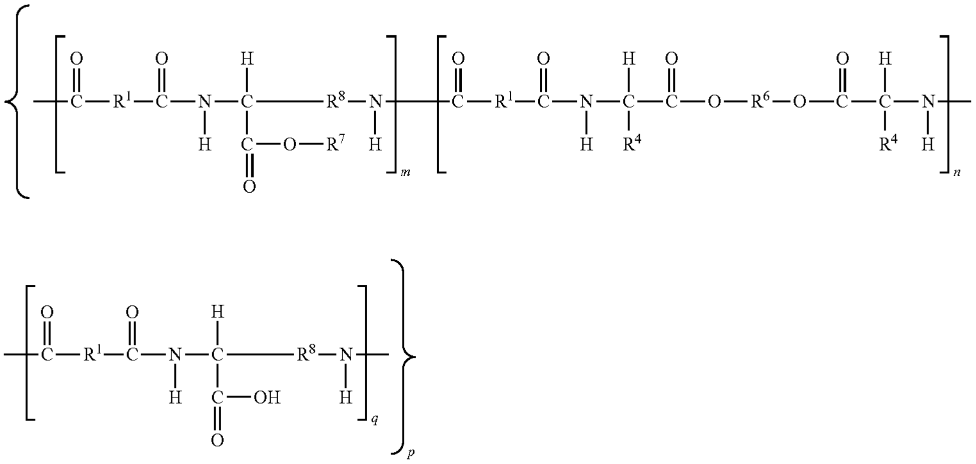

wherein m is from 0 to 0.20, n is from 0.80 to 0.95, q is from 0 to 0.20, and m+n+q=1, wherein m, n, and q represent the equivalents of the corresponding units in the random copolymer;

p is about 5 to about 300;

$R^1$ is $C_2$-$C_{20}$ alkylene;

$R^4$ is hydrogen, $(C_1$-$C_6)$alkyl, $(C_2$-$C_6)$alkenyl, $(C_2$-$C_6)$alkynyl, $(C_6$-$C_{10})$aryl, $—CH_2SH$, $—(CH_2)_2S(CH_3)$, $—CH_2OH$, $—CH(OH)CH_3$, $—(CH_2)_4NH_3+$, $—(CH_2)_3NHC(=NH_2+)NH_2$, $—CH_2COOH$, $—CH_2—CO—NH_2$, $—CH_2CH_2—CO—NH_2$, $—CH_2CH_2COOH$, $CH_3—CH_2—CH(CH_3)—$, $(CH_3)_2CH—CH_2—$, $H_2N—(CH_2)_4—$, $Ph-CH_2—$, $CH=C—CH_2—$, $(CH_3)_2CH—$, Ph-NH—,

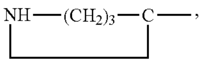 or 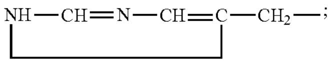

$R^6$ is according to Formula II or Formula III;

Formula II

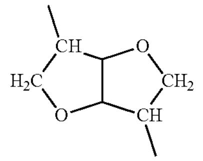

Formula III

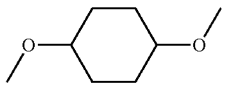

$R^7$ is $(C_6$-$C_{10})$aryl$(C_1$-$C_6)$alkylene; and $R^8$ is $C—C_8$ alkylene.

2. The random copolymer according to exemplary embodiment 1, wherein n is from 0.8 to 0.9.

3. The random copolymer of any one of the preceding exemplary embodiments, wherein m is 0-0.15 and q is 0-0.15.

4. The random copolymer of any one of the preceding exemplary embodiments, wherein m is 0.1-0.2.

5. The random copolymer of any one of the preceding exemplary embodiments, wherein m is 0.05-0.15.
6. The random copolymer of any one of the preceding exemplary embodiments, wherein the ratio m:q is from 5:1 to 1:5.
7. The random copolymer of any one of the preceding exemplary embodiments, wherein the ratio m:q is from 4:1 to 1:4.
8. The random copolymer of any one of the preceding exemplary embodiments, wherein m is greater than or equal to q.
9. The random copolymer of any one of the preceding exemplary embodiments, wherein q is 0.
10. The random copolymer of any one of the preceding exemplary embodiments, wherein p is from 50 to 200.
11. The random copolymer of any one of the preceding exemplary embodiments, wherein the random copolymer has a wet Tg of 36° C. or greater.
12. The random copolymer of any one of the preceding exemplary embodiments, wherein the random copolymer has a wet Tg of from 36° C., 36.5° C., 37° C., 37.5° C., 38° C., or 39° C. to 45° C., 44° C., 43° C., 42° C., 41° C., 40° C., 39° C., 38° C., or 37° C.
13. The random copolymer of any one of the preceding exemplary embodiments, wherein the initial wet Tg of the random copolymer and the wet Tg of the random copolymer after 35 days storage in PBS at 37° C. differ by at most +/−10%, +/−9%, +/−8%, +/−7%, +/−6%, or +/−5%.
14. The random copolymer of any one of the preceding exemplary embodiments, wherein q is from 0.05 to 0.20, the initial wet Tg of the random copolymer and the wet Tg of the random copolymer after 35 days in PBS at 37° C. differ by at most +/−10%, +/−9%, +/−8%, +/−7%, +/−6%, or +/−5%, and the Mn after 35 days in PBS at 37° C. is from 50%, 55%, 60%, or 65% to 70%, 75%, or 80% of the initial Mn.
15. The random copolymer of any one of the preceding exemplary embodiments, wherein $R_1$ is $—(CH_2)_8—$ or $—(CH_2)_4—$.
16. The random copolymer of any one of the preceding exemplary embodiments, wherein $R^4$ is hydrogen, $(C_1-C_6)$alkyl, $CH_3—CH_2—CH(CH_3)—$, $(CH_3)_2CH—CH_2—$, Ph-$CH_2$—, or $(CH_3)_2CH—$.
17. The random copolymer of any one of the preceding exemplary embodiments, wherein $R^6$ is according to Formula II.
18. The random copolymer of any one of the preceding exemplary embodiments, wherein $R^7$ is $C_6$aryl-$CH_2$—.
19. The random copolymer of any one of the preceding exemplary embodiments, wherein $R^8$ is $—(CH_2)_4—$.
20. The random copolymer of any one of the preceding claims, wherein the wet Tg is the initial wet Tg after soaking in PBS buffer solution at 37° C. for 4 days.
21. A drug delivery device comprising the random copolymer according to any one of the preceding exemplary embodiments and a bioactive agent.
22. The drug delivery device according to exemplary embodiment 21, wherein the drug delivery device is in the shape of a cylinder, a disc, or a spheroid.
23. The drug delivery device according to exemplary embodiment 21, wherein the drug delivery device is in the shape of a cylinder having a diameter of from 100, 150, 200, or 250 micrometers to 1000, 900, 800, 700, 600, or 500 micrometers.
24. The drug delivery device according to exemplary embodiment 21 or 23, wherein the drug delivery device is in the shape of a cylinder having a length of from 0.5, 1, 1.5, 2, 2.5, 3, 3.5, 4, 4.5 or 5 millimeters to 30, 25, 20, 15, 10, 5, 4, or 3 millimeters.
25. The drug delivery device according to exemplary embodiment 21, wherein the drug delivery device is in the shape of a cylinder having a diameter of from 1, 2, 3, 4, or 5 to 4, 5, 6, 7, 8, 9, or 10 mm.
26. The drug delivery device according to exemplary embodiment 21 or 25, wherein the drug delivery device is in the shape of a cylinder having a length of from 10, 15, 20, 25, or 30 mm to 150, 120, 100, or 80 mm.
27. The drug delivery device according to exemplary embodiment 21, wherein the drug delivery device is in the shape of a cylinder having a diameter of 1 to 5 mm and a length of from 20 to 100 mm.
28. The drug delivery device according to any one of the preceding exemplary embodiments, wherein the drug delivery device comprises a core comprising the random copolymer according to any one of the preceding exemplary embodiments and a bioactive agent, and a shell comprising a shell polymer.
29. The drug delivery device according to exemplary embodiment 28, wherein the shell polymer comprises poly(lactic acid), poly(glycolic acid), poly(lactide-co-glycolide), polycaprolactone, or a combination thereof.
30. The drug delivery device according to exemplary embodiment 28, wherein the shell polymer comprises the random copolymer according to any one of the preceding exemplary embodiments.
31. The drug delivery device according to any one of the preceding exemplary embodiments, wherein the drug delivery device is in the shape of a cylinder and comprises a cylindrical core and cylindrical shell.
32. The drug delivery device according to exemplary embodiment 31, wherein the cylindrical shell does not surround one end of the cylindrical core.
33. The drug delivery device according to exemplary embodiment 31, wherein the cylindrical shell does not surround both ends of the cylindrical core.
34. The drug delivery device according to any one of exemplary embodiments 28-33, wherein the shell does not comprise a bioactive agent.
35. An injectable formulation comprising a plurality of micro- or nano-particles comprising the random copolymer according to any one of exemplary embodiments 1-20 and a bioactive agent.
36. The injectable formulation according to exemplary embodiment 35, wherein the injectable formulation comprises a plurality of micro-particles comprising the random copolymer and a bioactive agent and having a mean particle diameter of from 10 to 500 micrometers.
37. The injectable formulation according to exemplary embodiment 35, wherein the injectable formulation comprises a plurality of micro-particles comprising the random copolymer and a bioactive agent and having a mean particle diameter of from 10, 20, 30, 40, 50, 60, 70, 80, 90, or 100 micrometers to 500, 475, 450, 425, 400, 375, 350, 325, or 300 micrometers.
38. The injectable formulation according to exemplary embodiment 35, wherein the injectable formulation comprises a plurality of nano-particles comprising the random copolymer and a bioactive agent and having a mean particle diameter of from 50, 100, 150, 200, 250, 300, 350, 400, 450, or 500 nanometers to 1000, 950, 900, 850, or 800 nanometers.

39. A medical device comprising a coating comprising the random copolymer according to any one of exemplary embodiments 1-20.
40. The medical device according to exemplary embodiment 39, further comprising a bioactive agent in the coating.
41. A medical device comprising a coating comprising a first layer and a second layer on the first layer, the first layer comprising the random copolymer according to any one of exemplary embodiments 1-20 and a bioactive agent, and the second layer comprising a second polymer.
42. The medical device according to exemplary embodiment 41, wherein the second polymer is the random copolymer according to any one of exemplary embodiments 1-20.
43. The drug delivery device, injectable formulation, or medical device according to any one of the preceding exemplary embodiments, wherein the bioactive agent is useful for treating glaucoma, ocular hypertension, wet age-related macular degeneration (AMD), diabetic retinopathy, diabetic macular edema, or other diseases of the eye.
44. The drug delivery device, injectable formulation, or medical device according to any one of the preceding exemplary embodiments, wherein the bioactive agent comprises latanoprost, bimatoprost, or travoprost.
45. The drug delivery device, injectable formulation, or medical device according to any one of the preceding exemplary embodiments, wherein the bioactive agent comprises latanoprost, bimatoprost, or travoprost at a loading of at least 10 wt %, 11 wt %, 12 wt %, 13 wt %, 14 wt %, or 15 wt %, based on the total weight of the (core) random copolymer plus bioactive agent.
46. The drug delivery device, injectable formulation, or medical device according to any one of the preceding exemplary embodiments, wherein the bioactive agent comprises latanoprost, bimatoprost, or travoprost at a loading of at most 30 wt % or 25 wt %, based on the total weight of the (core) random copolymer plus bioactive agent.
47. The drug delivery device, injectable formulation, or medical device according to any one of the preceding exemplary embodiments, wherein the bioactive agent comprises latanoprost, bimatoprost, or travoprost at a loading of at most 22 wt %, 21 wt %, 20 wt %, 19 wt %, 18 wt %, or 17 wt %, based on the total weight of the (core) random copolymer plus bioactive agent.
48. The drug delivery device, injectable formulation, or medical device according to any one of the preceding exemplary embodiments, wherein the bioactive agent comprises latanoprost, bimatoprost, or travoprost at a loading of from 11 wt % to 17 wt %, based on the total weight of the (core) random copolymer plus bioactive agent.
49. The drug delivery device, injectable formulation, or medical device according to any one of the preceding exemplary embodiments, wherein the bioactive agent is released for at least 100 days or at least 110 days in vitro.
50. The drug delivery device, injectable formulation, or medical device according to any one of the preceding exemplary embodiments, wherein the bioactive agent is released for at least 100 days or at least 110 days in vivo.
51. The drug delivery device, injectable formulation, or medical device according to any one of the preceding exemplary embodiments, wherein the bioactive agent is released for at most 180 days, at most 170 days, at most 160 days, at most 150 days, at most 140 days, at most 130 days, or at most 120 days in vitro.
52. The drug delivery device, injectable formulation, or medical device according to any one of the preceding exemplary embodiments, wherein the bioactive agent is released for at most 180 days, at most 170 days, at most 160 days, at most 150 days, at most 140 days, at most 130 days, or at most 120 days in vivo.
53. The drug delivery device, injectable formulation, or medical device according to any one of the preceding exemplary embodiments, wherein the bioactive agent comprises a chemotherapeutic, a JAK kinase inhibitors, an antipsychotic, or an antiviral.
54. The drug delivery device, injectable formulation, or medical device according to any one of the preceding exemplary embodiments, wherein the bioactive agent comprises one or more of Sorafenib, Pazopanib, Axitinib, Regorafenib, Cabozantinib, Lenvatinib, Sunitinib, Nintedanib, Crizotinib, Ceritinib, Alectinib, Brigatinib, Bosutinib, Dasatinib, Imatinib, Nilotinib, Ponatinib, Vemurafenib, Dabrafenib, Ibrutinib, Palbociclib, Ribociclib, Gefitinib, Erlotinib, Lapatinib, Afatinib, Osimertinib, or Trametinib.
55. The drug delivery device, injectable formulation, or medical device according to any one of the preceding exemplary embodiments, wherein the bioactive agent comprises one or more of Tofacitinib, Ruxolitinib, Oclacitinib, Baricitinib, Peficitinib, Fedratinib, Upadacitinib, Filgotinib, Cerdulatinib, Gandotinib, Lestaurtinib, Momelotinib, or Pacritinib.
56. The drug delivery device, injectable formulation, or medical device according to any one of the preceding exemplary embodiments, wherein the bioactive agent comprises one or more of Aripiprazole, Brexpiprazole, Olanzapine, Quetiapine, or Ziprasidone.
57. The drug delivery device, injectable formulation, or medical device according to any one of the preceding exemplary embodiments, wherein the bioactive agent comprises one or more of Tenofovir, Emtricitabine, Efavirenz, Elvitegravir, Cobicistat, Ribavirin, Daclatasvir, Sofosbuvir, Velpatasvir, Voxilaprevir, Glecaprevir, Pibrentasvir, Elbasvir, Grazoprevir, Simeprevir, or Ledipasvir.
58. The drug delivery device, injectable formulation, or medical device according to any one of the preceding exemplary embodiments, wherein the bioactive agent is a drug, a prodrug or co-drug thereof, a metabolite thereof, and/or a prodrug of the metabolite.
59. A method of treating a human or animal patient comprising the step of implanting in the patient the drug delivery device, injectable formulation, or medical device according to any one of the preceding exemplary embodiments.
60. A method of treating a human or animal patient suffering from glaucoma, ocular hypertension, wet age-related macular degeneration (AMD), diabetic retinopathy, or diabetic macular edema by implanting a drug delivery device according to any one of the preceding exemplary embodiments into the patient's eye.
61. A method of treating a human or animal patient suffering from glaucoma, ocular hypertension, wet age-related macular degeneration (AMD), diabetic retinopathy, or diabetic macular edema by implanting a drug delivery device according to any one of the preceding exemplary embodiments into an intracameral location in the patient's eye.

62. Use of a drug delivery device according to any one of the preceding exemplary embodiments for treating glaucoma, ocular hypertension, wet age-related macular degeneration (AMD), diabetic retinopathy, or diabetic macular edema.

63. A drug delivery device according to any one of the preceding exemplary embodiments for use in treating glaucoma, ocular hypertension, wet age-related macular degeneration (AMD), diabetic retinopathy, or diabetic macular edema.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A random copolymer according to Formula I:

Formula I

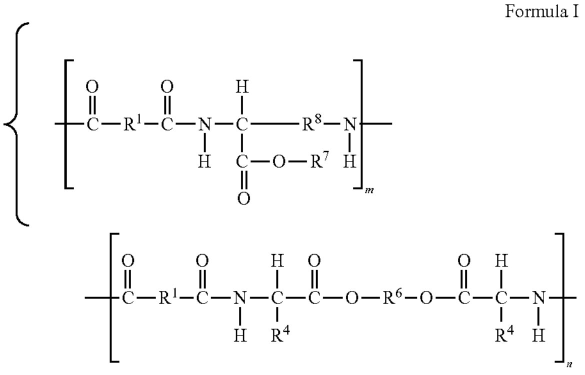

-continued

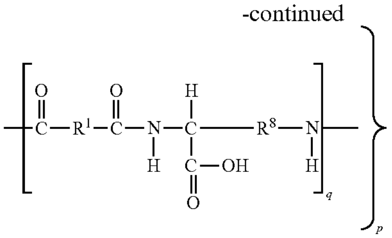

wherein m is from 0 to 0.20, n is from 0.80 to 0.95, q is from 0 to 0.20, and m+n+q=1, wherein m, n, and q represent the equivalents of the corresponding units in the random copolymer;

p is about 5 to about 300;

$R^1$ is $C_2$-$C_{20}$ alkylene;

$R^4$ is hydrogen, $(C_1$-$C_6)$alkyl, $(C_2$-$C_6)$alkenyl, $(C_2$-$C_6)$ alkynyl, $(C_6$-$C_{10})$ aryl, $—CH_2SH$, $—(CH_2)_2S(CH_3)$, $—CH_2OH$, $—CH(OH)CH_3$, $—(CH_2)_4NH_3+$, $—(CH_2)_3NHC(=NH_2+)NH_2$, $—CH_2COOH$, $—CH_2—CO—NH_2$, $—CH_2CH_2—CO—NH_2$, $—CH_2CH_2COOH$, $CH_3—CH_2—CH(CH_3)—$, $(CH_3)_2CH—CH_2—$, $H_2N—(CH_2)_4—$, $Ph$-$CH_2—$, $CH≡C—CH_2—$, $(CH_3)_2CH—$, Ph-NH—,

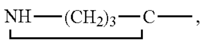, or 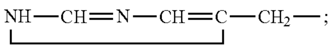;

$R^6$ is according to Formula II or Formula III;

Formula II

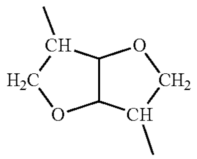

Formula III

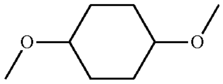

$R^7$ is $(C_6$-$C_{10})$ aryl$(C_1$-$C_6)$alkylene; and $R^8$ is $C_3$-$C_8$ alkylene, and wherein the random copolymer has a wet Tg of 37° C. or greater.

2. The random copolymer according to claim 1, wherein n is from 0.8 to 0.9.

3. The random copolymer according to claim 1, wherein m is 0-0.15 and q is 0-0.15.

4. The random copolymer according to claim 1, wherein q is 0.

5. The random copolymer according to claim 1, wherein the wet Tg is the initial wet Tg after soaking in PBS buffer solution for 4 days.

6. The random copolymer according to claim 1, wherein the random copolymer has a wet Tg of 37° C. to 44° C.

7. The random copolymer according to claim 1, wherein the initial wet Tg of the random copolymer and the wet Tg of the random copolymer after 35 days storage in PBS at 37° C. differ by at most +/−10%.

8. The random copolymer according to claim 1, wherein q is from 0.05 to 0.20, the initial wet Tg of the random copolymer and the wet Tg of the random copolymer after 35 days in PBS at 37° C. differ by at most +/−10% and the Mn after 35 days in PBS at 37° C. is at least 50% of the initial Mn.

9. The random copolymer according to claim 1, wherein $R^4$ is hydrogen, $(C_1-C_6)$alkyl, $CH_3—CH_2—CH(CH_3)—$, $(CH_3)_2CH—CH_2—$, Ph-$CH_2—$, or $(CH_3)_2CH—$.

10. The random copolymer according to claim 1, wherein $R^6$ is according to Formula II.

11. The random copolymer according to claim 1, wherein $R^7$ is $C_6$aryl—$CH_2$—.

12. A drug delivery device comprising the random copolymer according to claim 1 and a bioactive agent.

13. The drug delivery device according to claim 12, wherein the drug delivery device is in the shape of a cylinder having a diameter of from 1 to 10 mm and a length of from 10 to 150 mm.

14. The drug delivery device according to claim 12, wherein the drug delivery device comprises a core and a shell at least partially surrounding the core, wherein the core comprises the random copolymer and the bioactive agent, and the shell comprises a shell polymer which comprises the random copolymer.

15. The drug delivery device according to claim 12, wherein the bioactive agent is a drug, a prodrug or co-drug thereof, a metabolite thereof, and/or a prodrug of the metabolite.

16. The drug delivery device according to claim 12, wherein the bioactive agent comprises latanoprost, bimatoprost, or travoprost at a loading of from 11 wt % to 17 wt %, based on the total weight of the random copolymer plus bioactive agent.

17. The drug delivery device according to claim 12, wherein the bioactive agent is released for at least 100 days in vitro.

18. The drug delivery device according to claim 14, wherein the bioactive agent is released for at least 100 days in vivo.

19. A method of treating a human or animal patient comprising the step of implanting in the human or animal patient the drug delivery device according to claim 12.

20. A method of treating a human or animal patient suffering from glaucoma, ocular hypertension, wet age-related macular degeneration (AMD), diabetic retinopathy, or diabetic macular edema by implanting the drug delivery device according to claim 12 into an eye of the human or animal patient.

21. A method of treating a human or animal patient suffering from glaucoma, ocular hypertension, wet age-related macular degeneration (AMD), diabetic retinopathy, or diabetic macular edema by implanting the drug delivery device according to claim 12 into an intracameral location in an eye of the human or animal patient.

* * * * *